United States Patent
Woltermann

(10) Patent No.: US 11,351,371 B2
(45) Date of Patent: Jun. 7, 2022

(54) AUTOMATED CUSTOMIZATION OF OUTPUT INTENSITY FROM A FITNESS APPARATUS

(71) Applicant: Katalyst Inc., Tumwater, WA (US)

(72) Inventor: Björn Erich Woltermann, Seattle, WA (US)

(73) Assignee: Katalyst Inc., Tumwater, WA (US)

( * ) Notice: Subject to any disclaimer, the term of this patent is extended or adjusted under 35 U.S.C. 154(b) by 174 days.

(21) Appl. No.: 16/585,923

(22) Filed: Sep. 27, 2019

(65) Prior Publication Data

US 2020/0406101 A1 Dec. 31, 2020

Related U.S. Application Data

(60) Provisional application No. 62/866,395, filed on Jun. 25, 2019.

(51) Int. Cl.
*A63B 24/00* (2006.01)
*G11B 27/34* (2006.01)
(Continued)

(52) U.S. Cl.
CPC ....... *A61N 1/36034* (2017.08); *A61N 1/0452* (2013.01); *A61N 1/18* (2013.01); *A61N 1/36003* (2013.01); *A63B 24/0062* (2013.01); *A63B 24/0075* (2013.01); *A63B 71/0622* (2013.01); *G06F 16/9035* (2019.01); *G11B 27/34* (2013.01); *H04N 5/2222* (2013.01); *H04N 5/77* (2013.01); *H04N 21/439* (2013.01); *H04N 21/4325* (2013.01); *H04N 21/44* (2013.01);
(Continued)

(58) Field of Classification Search
None
See application file for complete search history.

(56) References Cited

U.S. PATENT DOCUMENTS 7,628,730 B1 * 12/2009 Watterson .............. A63B 22/02
482/8
10,170,153 B2 1/2019 Ekambaram et al.
(Continued)

OTHER PUBLICATIONS

Office Action for U.S. Appl. No. 16/585,717, dated Mar. 30, 2021, 16 Pages.
(Continued)

*Primary Examiner* — Sundhara M Ganesan
*Assistant Examiner* — Shila Jalalzadeh Abyaneh
(74) *Attorney, Agent, or Firm* — Lee & Hayes, P.C.

(57) ABSTRACT

An intensity of fitness apparatus output can be customized for a user during a workout session. A user profile of the user may be accessed to determine a starting intensity value at which output is to be provided by the user's fitness apparatus. Based on this starting intensity value and on command data associated with a workout session, an intensity profile for the user may be determined (e.g., created), which is usable for controlling an intensity of the output of the fitness apparatus during the workout session. While media content featuring an instructor conducting the workout session is output on an output device, the user's device may send commands to the fitness apparatus to control the intensity of the output of the fitness apparatus in accordance with the starting intensity value and, subsequently, the intensity profile of the user.

20 Claims, 11 Drawing Sheets

(51) Int. Cl.
  *A61N 1/36* (2006.01)
  *A63B 71/06* (2006.01)
  *A61N 1/18* (2006.01)
  *A61N 1/04* (2006.01)
  *H04N 21/8547* (2011.01)
  *H04N 5/222* (2006.01)
  *H04N 5/77* (2006.01)
  *G06F 16/9035* (2019.01)
  *H04N 21/432* (2011.01)
  *H04N 21/439* (2011.01)
  *H04N 21/44* (2011.01)
  *H04N 21/6587* (2011.01)
  *H04N 21/2187* (2011.01)

(52) U.S. Cl.
  CPC ....... *H04N 21/6587* (2013.01); *A61N 1/0484* (2013.01); *A63B 2024/0068* (2013.01); *A63B 2071/065* (2013.01); *A63B 2071/0625* (2013.01); *A63B 2213/004* (2013.01); *A63B 2220/806* (2013.01); *A63B 2220/808* (2013.01); *A63B 2225/20* (2013.01); *H04N 21/2187* (2013.01); *H04N 21/8547* (2013.01)

(56) References Cited

U.S. PATENT DOCUMENTS

| | | | |
|---|---|---|---|
| 10,798,468 B2 | 10/2020 | Bokowski et al. | |
| 2002/0077689 A1* | 6/2002 | Kirkland | A61N 1/0484 607/149 |
| 2006/0020174 A1* | 1/2006 | Matsumura | A61B 5/1123 600/300 |
| 2011/0319229 A1* | 12/2011 | Corbalis | A63B 71/0622 482/9 |
| 2016/0059079 A1* | 3/2016 | Watterson | G09B 19/0038 482/4 |
| 2018/0028810 A1* | 2/2018 | Schwarz | A61N 1/36031 |
| 2018/0036531 A1* | 2/2018 | Schwarz | A61N 1/0484 |
| 2018/0093121 A1* | 4/2018 | Matsuura | A63B 21/00185 |
| 2018/0268865 A1 | 9/2018 | Ekambaram et al. | |
| 2018/0304074 A1* | 10/2018 | Matsushita | A61N 1/36003 |
| 2018/0325452 A1* | 11/2018 | Woltermann | A61N 1/0452 |
| 2019/0020905 A1 | 1/2019 | Bennett | |
| 2019/0045278 A1 | 2/2019 | Ansari et al. | |
| 2019/0111318 A1* | 4/2019 | Evancha | A63B 71/0622 |
| 2019/0126099 A1* | 5/2019 | Hoang | A63F 13/798 |
| 2020/0236438 A1 | 7/2020 | Tagra et al. | |
| 2020/0252664 A1 | 8/2020 | Weinraub | |
| 2021/0178149 A1* | 6/2021 | Pisarev | A61N 1/36003 |

OTHER PUBLICATIONS

The PCT Search Report and Written Opinion dated Sep. 4, 2020 for PCT Application No. PCT/US20/39534, 8 pages.

Office Action for U.S. Appl. No. 16/585,717, dated Aug. 2, 2021, Wolterman, "Synchronizing Output From a Fitness Apparatus With Media Content", 22 pages.

International Preliminary Report on Patentability for PCT Application No. PCT/US20/39534, dated Jan. 6, 2022.

* cited by examiner

AUTOMATED CUSTOMIZATION OF OUTPUT INTENSITY FROM A FITNESS APPARATUS

CROSS REFERENCE TO RELATED APPLICATION

This application claims priority to commonly assigned, U.S. Provisional Patent Application Ser. No. 62/866,395, filed Jun. 25, 2019, entitled "SYSTEM TO SYNCHRONIZE THE TIMING AND CHARACTERISTICS OF MUSCULAR IMPULSES PROVIDED BY AN ELECTRO MUSCLE STIMULATION (EMS) DEVICE WITH MEDIA CONTENT," which is fully incorporated herein by reference.

BACKGROUND

Electrical Muscle Stimulation (EMS) is a technology that elicits muscle contraction using electrical impulses. The impulses are delivered via electrodes placed on the body near the muscles that are to be stimulated. EMS technology has been used to develop fitness products, such as EMS suits, which are designed to help users achieve their health and fitness goals, whether the goal is to burn calories, improve muscle tone, increase strength, and/or recover from an injury. When a user wears an EMS suit, the electrodes in the suit are situated near particular muscles groups (e.g., arms, legs, chest, abdominals, back, etc.) in order to deliver electric impulses targeted to those muscle groups while the user performs various exercise movements.

Existing EMS technology is such that an instructor and a user of an EMS suit are required to be collocated in the same environment to operate the EMS suit correctly. For example, a user typically visits a training facility to conduct a one-on-one EMS training session with an instructor. During the training session, which typically lasts about 20 minutes, the instructor demonstrates exercise movements and provides verbal instructions to the user wearing the EMS suit, and the user performs the exercise movements according to the instructor's directions while muscle contraction is elicited via the EMS suit. The instructor can monitor a countdown timer for an upcoming electrical impulse and may direct the user to start an exercise movement at the appropriate time (e.g., by saying "OK, let's do a squat in 3, 2, 1, go!"). A common electrical impulse pattern is a 4-second impulse (while the user performs an exercise movement), followed by a 4-second rest period. Throughout the session, the instructor may ask for feedback from the user as to whether the electrical impulse intensity is set to an appropriate level, and, if necessary, the instructor can make adjustments to increase or decrease the intensity of the electrical impulses. The instructor adjusts the impulse intensity by manually operating a nearby EMS control device that generates the electrical impulses. Accordingly, the instructor's physical presence allows for instructing the user to perform movements at the correct times and with proper form, and for controlling the electrical impulse intensity on behalf of the user. In this manner, the user can focus on performing the exercise movements, and the instructor can help guide the user through the session while adjusting the output of the EMS suit manually.

Discussed herein are technological improvements for, among other things, these devices and systems.

BRIEF DESCRIPTION OF THE DRAWINGS

The detailed description is described with reference to the accompanying figures. In the figures, the left-most digit(s) of a reference number identifies the figure in which the reference number first appears. The same reference numbers in different figures indicate similar or identical items.

DETAILED DESCRIPTION

Figure 1:
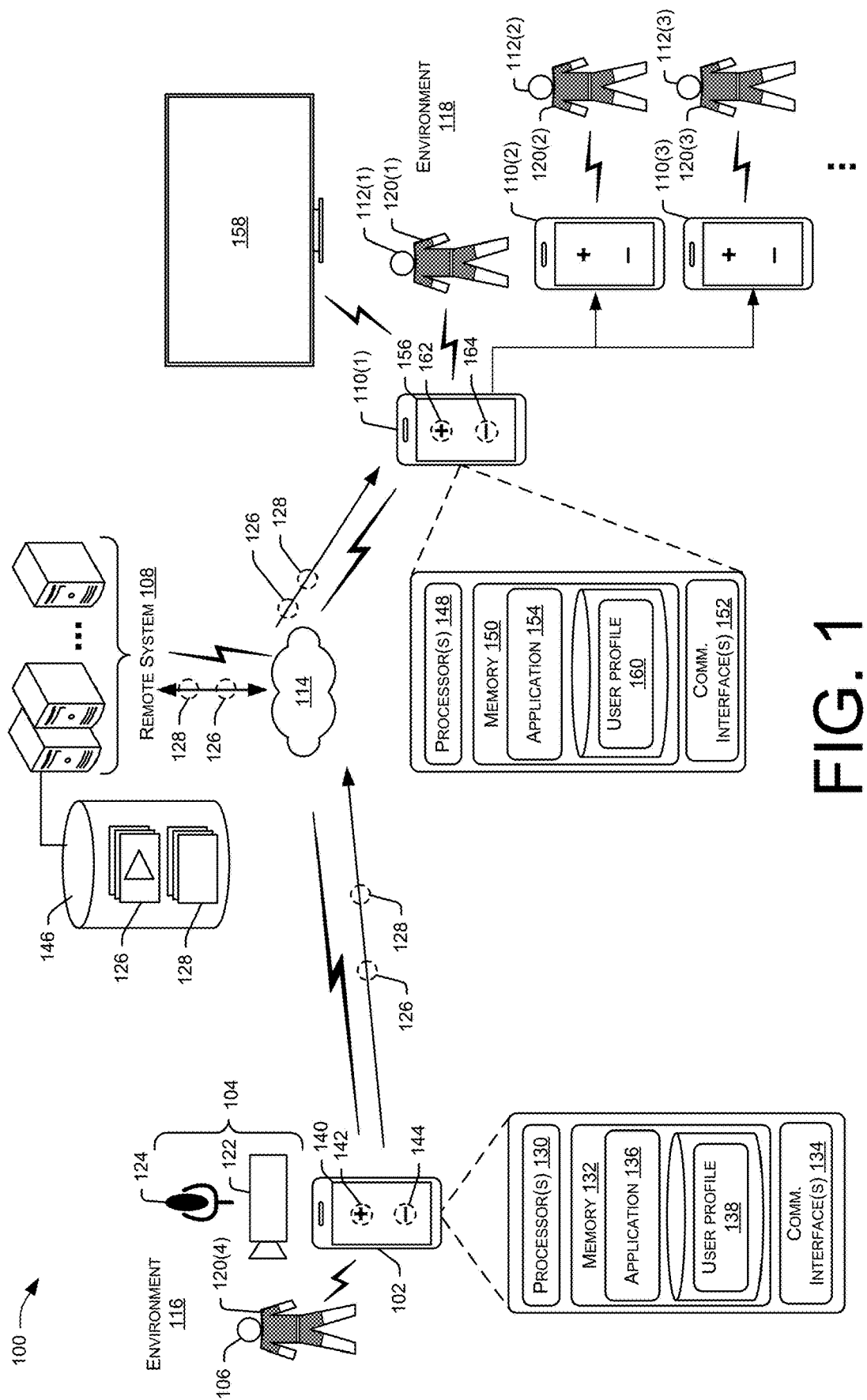
FIG. 1 is a schematic diagram of an illustrative system architecture, according to embodiments described herein.

This disclosure is directed to, among other things, systems, devices, and techniques for controlling the output of a fitness apparatus(es) in synchronization with media content. This synchronization allows an instructor to record a workout session at a different geographical location, and/or at a different (i.e., earlier) time, relative to the geographical location(s) where, and/or the time(s) when, a user(s) is/are following along with the instructor's directions and/or demonstrations exhibited in the media content. To illustrate, a user may possess a fitness apparatus that he/she can use to help achieve the user's health and fitness goals. Examples provided herein describe a fitness apparatus in the form of an electrical muscle stimulation (EMS) suit, which the user can wear his/her body, and which elicits muscle contraction using electrical impulses delivered via electrodes of the EMS suit. It is to be appreciated, however, that the fitness apparatuses described herein are not limited to EMS suits, and that the techniques and systems described herein may involve any suitable type of fitness apparatus (e.g., a stationary bicycle, a treadmill, etc.) that is configured to provide output that helps the user achieve his/her health and fitness goals.

In addition to possessing a fitness apparatus, a user may also possess a computing device that is configured to communicate with (e.g., send/receive data to/from) the fitness apparatus and with a remote system. The computing device may be separate from, or integrated into, the fitness apparatus. In either case, the computing device (sometimes shortened to "device" herein) may execute a client application that is configured to process command data associated with a workout session for purposes of synchronizing the output of the fitness apparatus with media content featuring the instructor conducting the workout session. For example, the client application may receive, from the remote system, media data corresponding to media content that features an instructor conducting a workout session, and the computing device may be configured to playback the media data for output of the media content on an output device in the user's environment. The client application may also receive, from the remote system, command data associated with the workout session. The command data may specify operations that are to be performed by the computing device, as well as timestamps within the media data to indicate times at which the operations are to be performed during playback of the media data on the computing device. At least some of these operations may comprise operations of sending commands to the fitness apparatus for controlling aspects of output provided by the fitness apparatus. In this manner, the output provided by the fitness apparatus is synchronized with the instructor's verbal directions and visual demonstrations exhibited in the media content so that the fitness apparatus output is timed correctly.

To illustrate, when playback of the media data is initiated on the computing device of the user, the client application may process the command data to determine the timestamps within the media data that drive the performance of the operations specified in the command data. Because the timestamps within the media data drive the performance of these operations, aspects of the output provided by the fitness apparatus can be provided in synchronization with the media content that is concurrently being output on an output device in the user's environment. Specifically, the timestamps specified in the command data may correspond to times in the media data when the instructor issues visible cues and/or audible cues, and the output of the fitness apparatus may be time-synchronized with these visible cues and/or audible cues. In examples where the fitness apparatus comprises an EMS suit, the user wearing the EMS suit can therefore feel electrical impulses delivered via electrodes of the EMS suit at appropriate times during the workout session, and for appropriate durations. To illustrate, when the media content depicts the instructor saying "OK, let's do a squat in 3, 2, 1, go!," the user's EMS suit may deliver an electrical impulse(s) at the same relative timestamp of the user's session as the instructor's EMS suit delivered a corresponding electrical impulse(s) in the instructor's session. This means that, when the user hears the instructor say the word "go" in the aforementioned verbal instructions of the media content, the user's EMS suit will deliver an electrical impulse(s), and the electrical impulse may cease at the start of the next rest period. The user may also see the instructor (in the media content) assuming a squat position at the time when the instructor says the word "go," which is the time when muscle contraction is elicited via the EMS suit. This time-synchronization is enabled by the computing device of the user sending a command to the fitness apparatus at, or near, the same relative time when the instructor said the word "go" during the instructor's session to initiate an electrical impulse(s) via an electrode(s) of the EMS suit at the correct time.

Also disclosed herein are techniques and systems for recording an instructor conducting a workout session while using a fitness apparatus in both pre-recording and live streaming production scenarios. To illustrate, an instructor may possess a fitness apparatus and a computing device that is configured to communicate with (e.g., send/receive data to/from) the fitness apparatus, as well as with a remote system. The computing device of the instructor may execute a client application that is configured to generate command data associated with the workout session. In addition, the instructor may utilize a recording device(s) to generate media data corresponding to media content featuring the instructor conducting the workout session. The command data and the media data may be time synchronized so that, when user computing devices process the command data, the fitness apparatuses of the users provide output that is synchronized with the instructor's visible cues and/or audible cues in the media content while the users are following along with the instructor's demonstrations and/or instructions exhibited in the media content. In a pre-recording scenario, the client application executing on the instructor's computing device may generate command data based at least in part on a predetermined sequence of output parameters, as well as on user input provided by the instructor during the workout session, and this command data may be uploaded along with the media data for on-demand access by users. In a live streaming scenario, a script of a workout session may be written in advance and used to generate command data that is uploaded to the remote system for access by users who wish to follow along with a live stream of the instructor conducting the workout session. The instructor may then record himself/herself conducting a workout session while following the script, and the recorded workout session may be live streamed over a network as a live stream of media data, with timestamps included in the live stream of media data to drive the performance of the operations that are specified in the command data. When such command data is processed on the computing devices of users who are following along with the live stream of the instructor, the user computing devices may send commands to respective fitness apparatuses of the users for controlling aspects of the output of the users' fitness apparatuses in synchronization with the live-streamed media content.

Also disclosed herein are techniques and systems for creating a customized intensity profile for a user of a fitness apparatus based at least in part on command data associated with a workout session, and for controlling the intensity of output provided by the user's fitness apparatus during a workout session in accordance with the customized intensity profile. For example, a client application executing on the user's computing device may access a user profile of the user to determine a starting intensity value at which output is to be provided by the user's fitness apparatus, and may initiate a workout session starting at an intensity level corresponding to the starting intensity value. The client application may also process the command data received from a remote system in order to determine an intensity profile of an instructor who conducted the workout session. Using the instructor's intensity profile, the client application may determine (e.g., by extrapolating a sequence of intensity values based on the starting intensity value and the instructor's intensity profile) a customized intensity profile for the user. In this manner, when the client application initiates playback of media data to output media content featuring the instructor conducting the workout session, the intensity of output provided by the user's fitness apparatus may follow along with the intensity adjustments the instructor is making to his/her fitness apparatus, as exhibited in the media content, while also providing the output at an intensity level(s) that is/are appropriate for the user (e.g., providing fitness apparatus output at the correct time, but at a fraction, or at a multiple, of the intensity of output provided by the instructor's fitness apparatus). In examples where the fitness apparatus is an EMS suit, the intensity of a user's muscle contraction(s) elicited by an electrical impulse(s) may be at an intensity level(s) that is/are personalized to the user of the EMS suit, while still controlling the electrical impulses in such a way that the muscle contractions follow along with the adjustments made to the instructor's fitness apparatus throughout the workout session. For instance, if the instructor increases the intensity of the electrical impulses delivered via the instructor's EMS suit at a particular time in the media content, the electrical impulses delivered via the user's EMS suit may also be increased at the particular time, but at a customized intensity level for the user, which may be a fraction of, or a multiple of, the intensity level for the instructor.

The techniques and systems described herein allow for providing a user of a fitness apparatus with a "hands-off" workout experience, notwithstanding the absence of a real-life instructor in the user's environment. For example, the user of a fitness apparatus may conduct a workout session in the comfort of his/her living room (or in any other environment) while following along with media content featuring an instructor, and while providing little-to-no user input to the user's computing device during the session so that the user can focus on performing the correct exercise movements. That is, the user can press "play" on his/her computing device, which is executing a client application, and the output provided by the user's fitness apparatus is automatically controlled in synchronization with the media content featuring an instructor of the workout session. Even though the system is capable of providing an entirely hands-off experience for the user, the user's computing device may nevertheless provide a user interface with an easy-to-use control mechanism for adjusting the intensity of output provided by the user's fitness apparatus, as desired by the user during the session. The user interface may, in some embodiments, provide additional mechanisms to control other parameters, such as pausing the playback of the media data, requesting to stop following the instructor's intensity profile, and the like.

The techniques and systems described herein also allow for recording and playback of workout sessions in high fidelity so that an instructor does not have to be physically present in the user's environment for the user to enjoy the same fidelity of instructions and information as if an instructor were physically present in the user's environment to guide the user through a workout session while making adjustments to the output of the fitness apparatus for the user. This high-fidelity experience is provided, at least in part, by the synchronization techniques described herein, whereby the output of the fitness apparatus is synchronized with the instructor's visible cues and/or audible cues exhibited in the media content. This allows for announcements of the instructor to be precisely timed with fitness apparatus output (e.g., EMS impulses) so that audio, video and fitness apparatus outputs are occurring at the correct times. The techniques and systems may achieve time synchronization between some or all output channels of video and/or audio, and fitness apparatus output over a duration of a workout session. For instance, in examples where media data is pre-recorded and subsequently accessed by a user on-demand, the user is able to see, hear, and feel aspects of the workout session as it happened during the recording of the workout session by the instructor. The user can also be provided with a consistent experience regardless of where and/or when the user is conducting the workout session, and regardless of whether the computing device of the user is online or offline, and/or whether the computing device is receiving the media data as a live data stream in real-time, or as a pre-recorded data stream on-demand. This is at least because the visible cues and/or audible cues of the instructor exhibited in the media content are synchronized with the output of the fitness apparatus so that the sensations the user sees, hears and feels are timed correctly. Furthermore, the fitness apparatus output may be controlled in accordance with the instructor's intensity profile, as if the instructor were making the adjustments to the intensity of output provided by the user's fitness apparatus, while also providing the fitness apparatus output for the user at an intensity level that is customized to the user.

In some embodiments, the techniques and systems described herein allow for live streaming of workout sessions with the instructor in one geographical location and a user(s) in one or more other geographical locations, while ensuring little-to-no lag between the visual, auditory, and sensory experience of the user(s). The instructor can also make changes in fitness apparatus output parameters during a given workout session to enable the combination of training goals and modalities in one seamless session.

A user friendly, at-home fitness system is described herein where a user of a fitness apparatus can make adjustments via an easy-to-use interface of a computing device (e.g., by making binary adjustments, such as up or down) to customize the user's workout experience. This allows unsophisticated users to operate the system with ease, and for different types of users at different experience levels and/or fitness conditions to perform the same workout, but at respective intensity levels that are appropriate for each of them. For example, a senior citizen and a professional football player can conduct the same workout, at customized intensity levels of fitness apparatus output.

The techniques and systems described herein may also allow for one or more devices to conserve resources with respect to communications bandwidth resources, processing resources, memory resources, power resources, and/or other resources, as described herein. Additional technical effects can also be realized from an implementation of the technologies disclosed herein. Described herein are example processes, as well as systems and devices comprising one or more processors and one or more memories, as well as non-transitory computer-readable media storing computer-executable instructions that, when executed, by one or more processors perform various acts and/or processes disclosed herein.

FIG. 1 is a schematic diagram of an illustrative system architecture 100, according to embodiments described herein. The system architecture 100 may include a first computing device 102 and a recording device(s) 104 used by an instructor 106 while the instructor 106 is conducting a workout session. The system architecture 100 may also include a remote computing system 108 (sometimes referred to herein as a "remote system 108"), and one or more second computing devices 110 used by one or more corresponding users 112 during performance of a workout session by the user(s) 112. The instructor's 106 computing device 102 may couple with the remote system 108 and/or with the computing device(s) 110 over a network 114. The network 114 may represent and/or include, without limitation, the Internet, other types of data and/or voice networks, a wired infrastructure (e.g., coaxial cable, fiber optic cable, etc.), a wireless infrastructure (e.g., radio frequencies (RF), cellular, satellite, etc.), and/or other connection technologies. The computing device(s) 110 of the user(s) 112 may also couple with the remote system 108 and/or with the computing device 102 over the network 114. In general, this system architecture 100 allows for the instructor 106 to record himself/herself conducting a workout session in a first environment 116 (e.g., a studio production environment, a fitness center, a training facility, etc.) that is geographically remote from a second environment 118 (e.g., a home, an office, etc.) where the user(s) 112 are following along with the instructor's 106 recorded workout session, either in a live streaming scenario, or by accessing a pre-recorded workout session on-demand.

The instructor 106 and the user(s) 112 are also shown as having/possessing respective fitness apparatuses 120. The fitness apparatuses 120 may include any suitable type of fitness apparatus that is configured to provide output to help achieve the user's health and fitness goals. In the example of FIG. 1, the fitness apparatuses 120 possessed by the instructor 106 and by the users 112 are in the form of electrical muscle stimulation (EMS) suits. An EMS suit can be worn on the human body, and, when operated, the EMS suit may elicit muscle contraction using electrical impulses delivered via electrodes of the EMS suit. Although the examples herein are predominantly described with regard to EMS suits, it is to be appreciated, however, that the fitness apparatuses 120 described herein are not limited to EMS suits, and may represent any suitable type of fitness apparatus 120 that is configured to provide output that helps the user of the fitness apparatus 120 achieve his/her health and fitness goals. Accordingly, the fitness apparatuses 120 described herein may include, without limitation, wearable fitness apparatuses (e.g., EMS suits, fitness watches, fitness bands, etc.), treadmills, stationary bicycles, elliptical machines, rowing machines, stair climbers, exercise pools (e.g., swimming machines), weight machines, and/or similar types of fitness apparatuses 120. Moreover, it is to be appreciated that the fitness apparatuses 120 described herein may be built/designed for cardiovascular exercise, strength exercise, and/or flexibility exercise, or the like, and the fitness apparatuses 120 can be used in various environments and settings, including, without limitation, household fitness settings (at-home workouts), medical rehabilitation settings, corporate offices, outdoor environments, and the like. It is also to be appreciated that, regardless of the type of fitness apparatuses 120 used, the instructor 106 and the user(s) 112 may utilize the same type of fitness apparatus 120 for a given workout session that is recorded by the instructor 106 and consumed by the user(s) 112, as opposed to using different types of fitness apparatuses.

Figure 2:
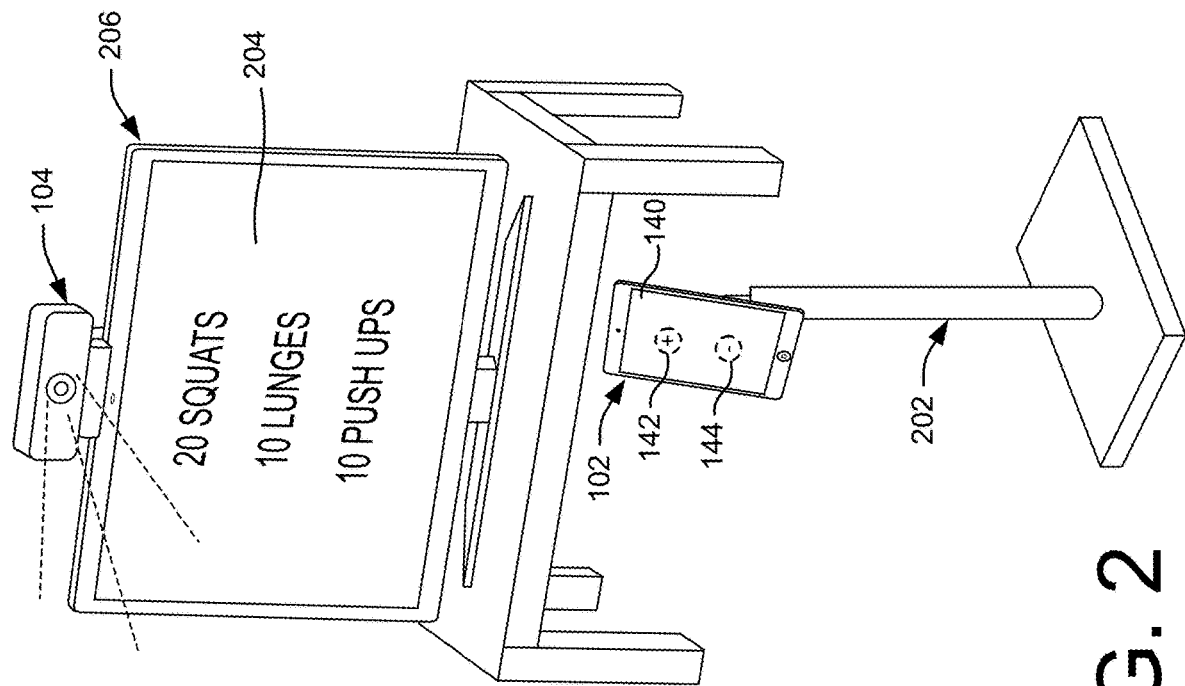
FIG. 2 illustrates an instructor who is in the process of recording a workout session while using a fitness apparatus. A nearby computing device is used to generate command data for use in controlling fitness apparatus output in accordance with the workout session.
Figure 2:
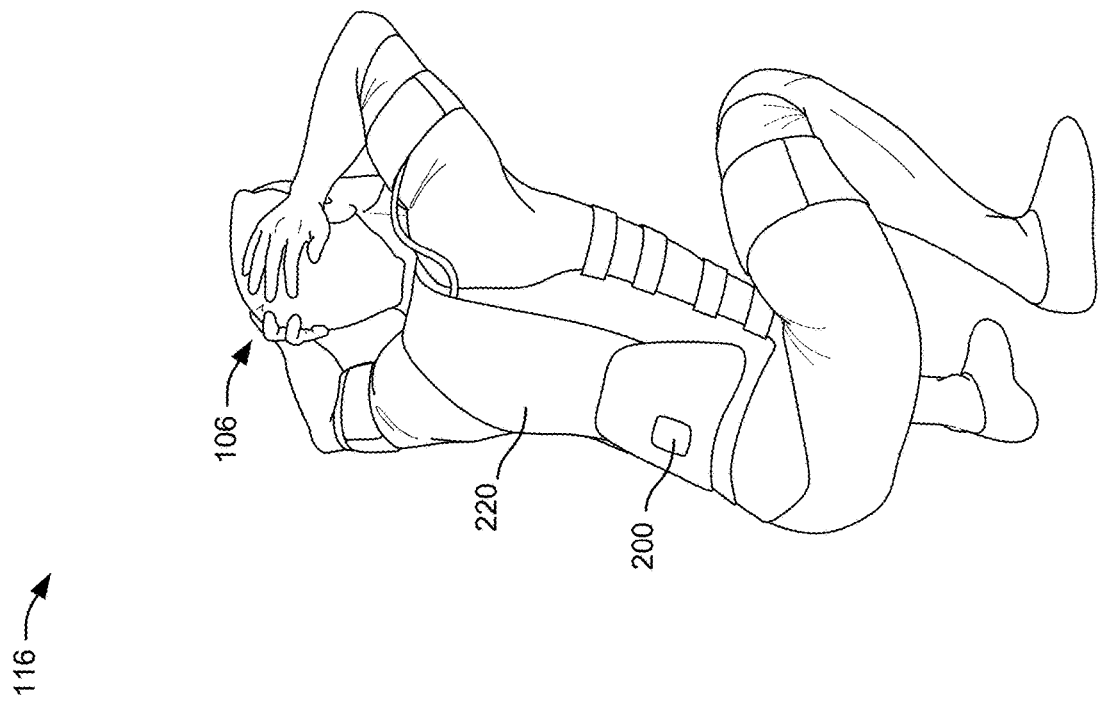
Figure 3:
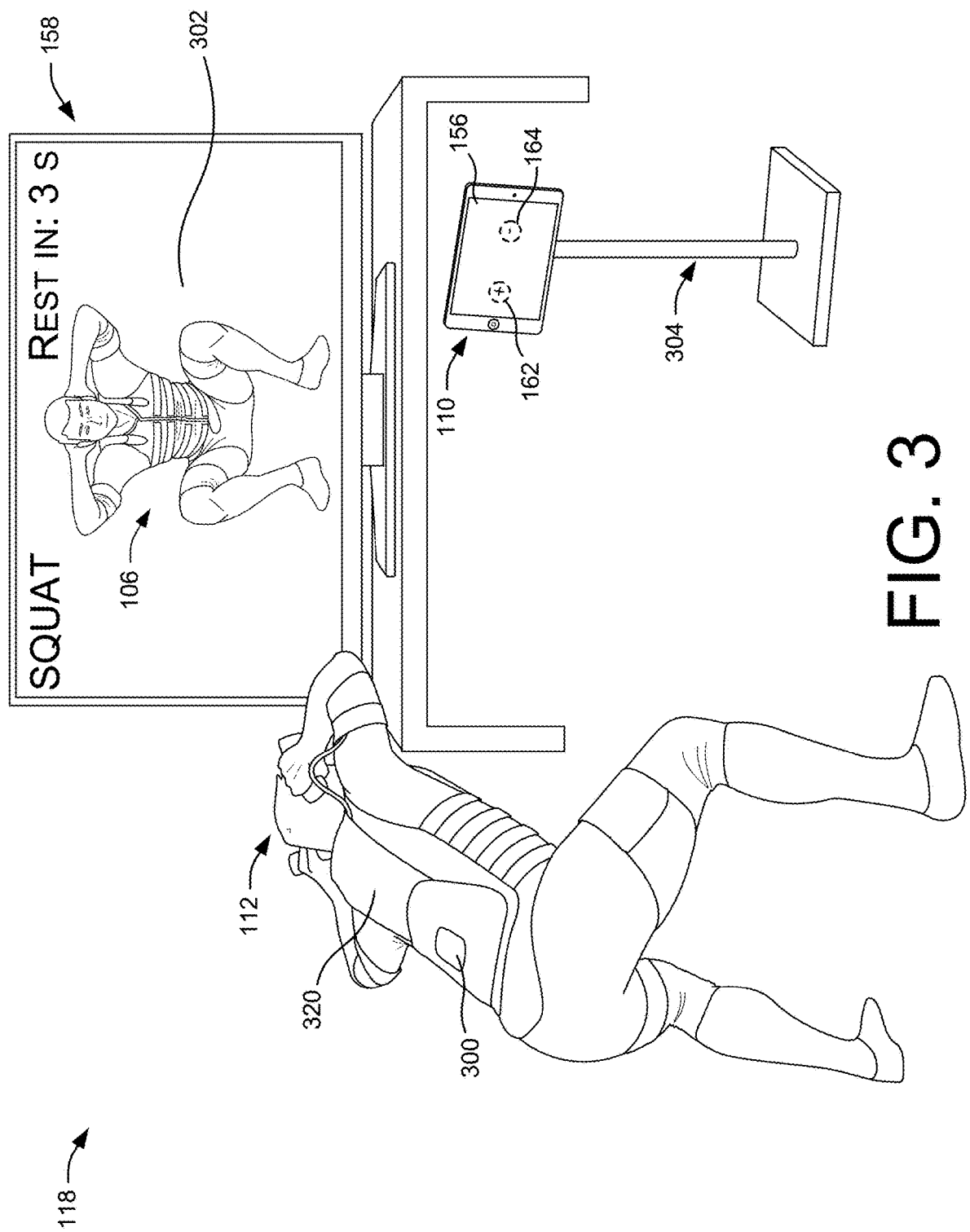
FIG. 3 illustrates a user who is using a fitness apparatus to exercise while following along with media content featuring an instructor conducting a workout session. Output of the fitness apparatus is being controlled by a nearby computing device so that the output is provided in synchronization with the media content.

Referring briefly to FIG. 2, an instructor 106 is shown as wearing an EMS suit 220. Meanwhile, FIG. 3 shows a user 112 wearing an EMS suit 320. As mentioned, an EMS suit 220/320 is an example of a fitness apparatus 120. An EMS suit 220/320 may generally include a vest portion that is worn on the upper torso, as well as arm portions (e.g., arm bands) that are worn on the arms, and leg portions (e.g., leg bands) that are worn on the legs, and possibly parts of the lower torso. These portions of the EMS suit 220/320 may be coupled via electrical wires, and one or more electrodes may be situated in the EMS suit 220/320 at fixed locations relative to the EMS suit 220/320 so that, when the EMS suit 220/320 is worn, the electrodes are positioned on the body at a location of a targeted muscle group. A layer of base material (e.g., an undergarment) may be worn between the electrode(s) and the skin. In some embodiments, gel and/or water and/or similar materials may be interposed between the electrode(s) and the base layer of material to improve electrical conductivity. The EMS suit 220/320 may include an EMS device 200/300 (sometimes referred to herein as an "impulse pack 200/300") that includes one or more processors to deliver electrical impulses via the electrode(s) of the EMS suit 220/320 for eliciting a muscle contraction. The processor(s) of the impulse pack 200/300 is/are configured to process computer-executable instructions and/or data (e.g., EMS commands received from a nearby computing device) that cause the electrode(s) to deliver an impulse(s) to one or more muscle group(s) in accordance with specified output parameters. For example, these instructions and/or data may specify impulses in terms of an amount of voltage, current, a period of time, a frequency, etc.

The instructor 106 may represent a qualified (e.g., certified) and/or experienced individual who is trained to perform and/or teach proper exercise techniques for a given workout session involving a fitness apparatus 120. For example, the instructor 106 may be a qualified trainer of EMS workout sessions (e.g., training sessions) to provide proper exercise techniques for a workout involving an EMS suit 220/320. To record a workout session (e.g., an EMS training session) for consumption by one or more users 112 in real-time, or at a later time on-demand, the instructor 106 may utilize a recording device(s) 104 and a computing device 102. The recording device(s) 104 may include a camera(s) 122 to record image data and a microphone(s) 124 to record audio data. The camera(s) 122 and the microphone(s) 124 can be part of the same recording device 104, such as a video camera with a built-in microphone(s) (e.g., microphone array), or these components may be separate recording devices used together (e.g., a boom microphone used with a video camera), and/or the recording device 104 may include one or the other (e.g., an audio recording device, an image recording device, etc.). That is, in some embodiments, the instructor 106 may record audio data of a workout session using the microphone(s) 124, without using a camera to record image data, or the instructor 106 may record image data of a workout session using the camera(s) 122, and without using a microphone to record audio data. The examples described herein often describe a scenario where media data 126 is generated by recording both image data using a camera(s) 122 and audio data using a microphone(s) 124. As such, the media data 126 generated by the recording device(s) 104 may include both image data and audio data (e.g., a video file(s)). The media data 126 may include timestamps corresponding to different points within the recording. When this media data 126 is played back on a computing device, the corresponding media content (e.g., video content, image content, audio content, etc.) may be output on an output device(s) (e.g., display(s), speaker(s), etc.).

The instructor's 106 computing device 102 may represent a personal computing device, such as a tablet computer, although the computing device 102 is not limited to a configuration of a tablet. That is, the computing device 102 can be implemented as any suitable type of computing device including, without limitation, a personal computer (PC), a desktop computer, a laptop computer, a mobile phone (e.g., a smart phone), a tablet computer, a portable digital assistant (PDA), a wearable computer, and/or any similar computing device 102. In accordance with various embodiments described herein, the terms "computing device," "personal computing device," "personal computer," "computer," "mobile device," "wireless device," "communication device," "wireless communication device," "wireless terminal," "mobile terminal," "user device," "user equipment (UE)," "client device," "client computing device," "computer display device," and "device," may be used interchangeably herein to describe any computing device 102 that is capable of executing applications, generating command data 128 (described in more detail below), and communicating with (e.g., send/receive data to/from) other devices, such as the fitness apparatus 120(4) and/or the remote system 108.

The computing device 102 is shown as including one or more processors 130, memory 132 (or non-transitory computer-readable media 132), and a communications interface(s) 134. In some implementations, the processors(s) 130 may include a central processing unit(s) (CPU(s)), a graphics processing unit(s) (GPU(s)), both CPU(s) and GPU(s), a microprocessor(s), a digital signal processor(s) or other processing units or components known in the art. Alternatively, or in addition, the functionally described herein can be performed, at least in part, by one or more hardware logic components. For example, and without limitation, illustrative types of hardware logic components that can be used include field-programmable gate arrays (FPGAs), application-specific integrated circuits (ASICs), application-specific standard products (ASSPs), system-on-a-chip systems (SOCs), complex programmable logic devices (CPLDs), etc. Additionally, each of the processor(s) 130 may possess its own local memory, which also may store program modules, program data, and/or one or more operating systems.

The memory 132 may include volatile and nonvolatile memory, removable and non-removable media implemented in any method or technology for storage of information, such as computer-readable instructions, data structures, program modules, or other data. The memory 132 may be implemented as computer-readable storage media ("CRSM"), which may be any available physical media accessible by the processor(s) 130 to execute instructions stored on the memory 132. In one basic implementation, CRSM may include random access memory ("RAM") and Flash memory. In other implementations, CRSM may include, but is not limited to, read-only memory ("ROM"), electrically erasable programmable read-only memory ("EEPROM"), compact disc (CD)-ROM, digital versatile disks (DVD) or other optical storage, magnetic cassettes, magnetic tape, magnetic disk storage or other magnetic storage devices, RAID storage systems, or any other tangible medium which can be used to store the desired information and which can be accessed by the processor(s) 130.

The communication interface(s) 134 may be configured to facilitate a wireless and/or wired connection to a network and/or to another device(s). The communication interface(s) 134 may implement multiple types of wireless or radio technologies, such as a radio that is configured to operate as a Bluetooth radio (e.g., Bluetooth Low Energy (BLE) radio), a Wi-Fi radio, a cellular radio, and/or combinations thereof. Therefore, in at least some embodiments, the communication interface(s) 134 may comprise a wireless communication interface (e.g., wireless radio). It is to be appreciated that the communication interface(s) 134 may further include physical ports to facilitate a wired connection to a network, a connected peripheral device, or a plug-in network device that communicates with other wireless networks. In FIG. 1, the computing device 102 is shown as being wirelessly coupled to the fitness apparatus 120(4) used by the instructor 106. This allows the computing device 102 to send commands to the fitness apparatus 120(4) to control an aspect of output provided by the fitness apparatus 120(4). For example, a command may be sent wirelessly via the communication interface(s) 134 to control the initiation of an electrical impulse(s), the cessation of an electrical impulse(s), or adjustment of an intensity of an electrical impulse(s) delivered via an electrode(s) of the instructor's 106 EMS suit 220. For other types of fitness apparatuses, such as a stationary bicycle, similar commands may be sent to the fitness apparatus 120 to control an aspect of the output, such as the initiation of resistance (i.e., making it harder for the instructor 106 to pedal the bicycle), the cessation of the resistance, adjustment of an intensity of the resistance. For a treadmill, a command may be sent to the fitness apparatus 120 to control the incline of the treadmill so that gravity works against the instructor 106, making it harder for the instructor 106 to walk or run. One can appreciate that a variety of types of fitness apparatuses 120 with varying output parameters can be controlled in these and similar manners. It is also to be appreciated that the computing device 102 may, in some embodiments, be integrated into the fitness apparatus 120(4) such that data is merely sent over a wire to a processor(s) of the fitness apparatus 120(4) to control aspects of the output provided by the fitness apparatus 120(4).

The instructor's 106 computing device 102 is shown as having a client application 136 installed in the memory 132. The client application 136 may represent an executable application (e.g., code, computer-executable instructions, etc.) that is configured to generate and send commands to the fitness apparatus 120(4) for controlling aspects of the output provided by the fitness apparatus 120(4), and to generate command data 128, as well as send the command data 128 and media data 126 (generated using the recording device(s) 104) to the remote system 108. For example, the client application 136 may be programmed with a predetermined sequence of output parameters for controlling (e.g., steering) the output of the fitness apparatus 120(4) over the duration of a workout session. In embodiments where the fitness apparatus 120(4) represents an EMS suit 220 worn by the instructor 106, the predetermined sequence of output parameters may correspond to timed EMS impulses (e.g., an impulse for a duration of 4 seconds followed by a 4-second rest period). It is to be appreciated that any amount of time can be programmed for the impulse and rest periods of an EMS workout session, and this disclosure is not limited to the example time periods provided herein. To initiate an electrical impulse, the client application 136 may wirelessly send a command to the EMS suit 220, and the impulse pack 200 of the EMS suit 220 may receive and process the received command to deliver a corresponding electrical impulse via one or more electrodes of the EMS suit 220 (e.g., electrodes that are positioned on the instructor's 106 chest to elicit muscle contraction of the pectoral muscles). Before, during, and/or after an electrical impulse, the instructor 106 may demonstrate an exercise movement(s) (e.g., a squat, a lunge, an upright shoulder press, a punching motion, a kicking motion, etc.) by demonstrating the correct/ proper execution of individual exercises and by going through at least some of the same motions the user(s) 112 is/are instructed to perform. Before, during, and/or after an electrical impulse, the instructor 106 may also utter verbal directions, instructions, guidance, and/or recommendations explaining each exercise movement, as well as motivational words or phrases for the user(s) 112. Before initiation of an electrical impulse, the instructor 106 may announce the start of the impulse to help the user(s) 112 flex his/her muscles in time for the correct execution of the exercise to help the user(s) 112 find the right timing and rhythm. During an impulse, the instructor 106 may count down the number of repetitions until a next rest period.

A user profile 138 of the instructor 106 may be stored in the local memory 132 of the computing device 102 and/or at the remote system 108 for access by the computing device 102. The user profile 138 may specify user data that is personal to the instructor 106, such as information about the instructor 106 (e.g., his/her name, contact info, height, weight, fitness condition, experience level, etc.), and this information may include a history of output parameters for the fitness apparatus 120(4) associated with previous workout sessions involving the instructor 106. For example, the user profile 138 may specify a sequence of intensity values at which output was provided by the fitness apparatus 120(4) over a duration of a previous workout session conducted by the instructor 106 at a time in the past. For example, in a previous workout session, the instructor 106 may have started the session at time $t_1$ with an overall electrical impulse intensity of 90 (here, "90" represents an arbitrary unit of measurement), followed by an increase to an intensity of 100 at time $t_2$, followed by an increase to an intensity of 105 at a subsequent time, and so on and so forth. The resulting sequence of intensity values may be saved in the user profile 138 of the instructor 106, and this sequence of intensity values is sometimes referred to herein as an "intensity profile." It is to be appreciated that the user profile 138 of the instructor 106 can maintain multiple intensity profiles that correspond to multiple past workout sessions conducted by the instructor 106.

The instructor 106 may provide credentials (e.g., username, password, biometric data, etc.) to log into the client application 136 so that the client application 136 is authorized to access the user profile 138 of the instructor 106. The client application 136 may provide a user interface for the instructor 106 to start a new workout session that is to be recorded for consumption by one or more users 112 in real-time or on-demand at a later time. The client application 136 may be configured with a plurality of pre-programmed sequences of output parameters for different workout sessions that the instructor 106 can select. Additionally, or alternatively, the instructor 106 may specify a customized workout session in terms of its overall duration, the timing, intensity, frequency, and/or duration of impulses that are to be provided, etc. In this manner, a predetermined sequence of output parameters for controlling the output of the fitness apparatus 120(4) over the duration of the to-be-recorded workout session can be followed by the client application 136 once the instructor 106 starts the workout session.

The instructor 106, or another user assisting the instructor 106, can provide user input (e.g., select a button, such as a physical button on the recording device(s) 104 or a soft button on a touch screen of the recording device(s) 104), issue a voice command, etc.) to start recording the workout session via the recording device(s) 104. Over the duration of the workout session, the recording device(s) 104 may generate media data 126 (e.g., a video file(s)) that corresponds to media content (e.g., video content) featuring the instructor 102 conducting the workout session. In addition, the instructor 106, or another user assisting the instructor 106, can provide user input (e.g., select a button, such as a physical button on the device 102 or a soft button on a touch screen of the device 102), issue a voice command, etc.) to start controlling the output of the fitness apparatus 120(4) in accordance with the predetermined sequence of output parameters and to start generating command data 128 based on those output parameters. The client application 136 may access the user profile 138 of the instructor 106 to determine a starting intensity value at which the output is to be provided by the fitness apparatus 120(4) so that the intensity profile is customized to the instructor 106 by providing output via the fitness apparatus 120(4) at an appropriate intensity level. The starting intensity value may be based on a starting intensity value of a past (e.g., previous) workout session, as indicated in the user profile 138, or it may be a default starting intensity value if there is no history on the instructor 106.

Furthermore, the computing device 102 may provide a user interface for the instructor 106 to adjust the intensity of the output provided by the fitness apparatus 120(4) at one or more times during the workout session. This user interface can be provided in any suitable manner, such as a voice user interface (VUI), a graphical user interface (GUI), etc. FIG. 1 shows the computing device 102 as including a display 140, and the client application 136 as presenting, on the display 140, a first selectable element 142 (e.g., a "plus" icon) and a second selectable element 144 (e.g., a "minus" icon). The first selectable element 142, upon selection, may cause the device 102 to send a command to the fitness apparatus 120(4) to increase a current intensity level at which the output is provided by the fitness apparatus 120(4) to an increased intensity level. The second selectable element 144, upon selection, may cause the device 102 to send a command to the fitness apparatus 120(4) to decrease a current intensity level at which the output is provided by the fitness apparatus 120(4) to a decreased intensity level. As such, if the instructor 106 feels like the intensity of the output provided by the fitness apparatus 120(4) is too much, the instructor 106 can provide user input to the computing device 102 (e.g., by selecting the second selectable element 144) to decrease the output provided by the fitness apparatus 120(4) at any time that the instructor 106 desires to do so. Conversely, if the instructor 106 feels like the intensity of the output provided by the fitness apparatus 120(4) is not enough, the instructor 106 can provide user input to the computing device 102 (e.g., by selecting the first selectable element 142) to increase the output provided by the fitness apparatus 120(4) at any time that the instructor 106 desires to do so. This user input (i.e., intensity level adjustments) can be recorded by the client application 136 and merged with the predetermined sequence of output parameters to generate command data 128 for a workout session that includes both a predetermined sequence of output parameters, and output parameters that are based on the instructor's 106 intensity level adjustments.

The command data 128 (sometimes referred to herein as "telemetry data 128") generated by the client application 136 may be time synchronized with the media data 126 this is generated using the recording device(s) 104. For instance, the command data 128 may specify operations that are to be performed by a user's 112 computing device 110 during playback of the media data 126 on the user's 112 computing device 110, as well as timestamps within the media data 126 at which the operations are to be performed during playback of the media data 126 on the user's 112 computing device 110. In this manner, the operations specified in the command data 128 are driven by the timestamps in the media data 126 so that the operations are synchronized with the visual demonstrations and/or verbal utterances of the instructor 106 exhibited in the media content. That is, the operations in the command data 128 are specified relative to particular timestamps in the media data 126. At least some of the operations specified in the command data 128 include operations of sending commands to a nearby fitness apparatus 120 to control aspects of output provided by the fitness apparatus 120. Because these operations correspond to telemetry data that was recorded by the client application 136 while the instructor 106 conducted the workout session (e.g., telemetry data regarding the adjustments to the intensity of the output provided by fitness apparatus 120(4)), the command data 128 can be referred to as "telemetry data 128" herein. At least some of the operations specified in the command data 128 may represent a sequence of intensity values (an intensity profile) associated with the user profile 138 of the instructor 106. In this sense, the command data 128 reflects the commands sent by the client application 136 to the fitness apparatus 120(4) to control aspects of the output provided by the fitness apparatus 120(4), and these commands include commands pertaining to adjustments that the instructor 106 provided in real-time during the workout session by adjusting the intensity of the output provided by the fitness apparatus 120(4).

In some embodiments, the command data 128 may further include operations of presenting graphical information that is to be overlaid atop the media content featuring the instructor 106 conducting the workout session. Such graphical overlays may be presented at appropriate times during the playback of the media data 126 and may convey information, such as the name of the exercise movement (e.g., "Squat", "Lunge", etc.), time information (e.g., a countdown to the initiation or the cessation of an electrical impulse, the elapsed time and/or remaining time of the workout session, etc.), information to indicate whether an electrical impulse is on or off, and similar information. Accordingly, the operations specified in the command data 128 may instruct a client application 154 of a user device 110 to perform operations A, B, and C at time, t=4 seconds, to perform operations X, Y, and Z at time, t=8 seconds, and so on and so forth. These operations may relate to sending commands to the fitness apparatus 120, displaying graphical overlays atop the media content, and/or similar operations that are performed at times relative to the timestamps in the media data 126.

In some embodiments, the command data 128 may be generated as a file(s) in any suitable format. For example, the command data 128 may be generated as a JavaScript Object Notation (JSON) file(s), which is/are executable by the computing devices 110 of users 112 during playback of the media data 126 on the computing devices 110. The command data 128 (e.g., a file(s)) may be stored in the memory 132 of the instructor's 106 computing device 102. Alternatively, the command data 128 may be generated as an Extensible Markup Language (XML) file, a YAML Ain't Markup Language (YAML) file, a comma-separated values (CSV) file, a plain text file, or an array data structure. In addition, the media data 126 (e.g., a file(s), such as a video file(s), an audio file(s), etc.) may be stored in the memory 132 of the instructor's 106 computing device 102, such as when the media data 126 is transferred from the recording device(s) 104 to the computing device 102 (e.g., over a wired or wireless connection for file transfer).

It is to be appreciated that time synchronization between the command data 128 and the media data 126 may involve some human intervention, such as an editor going through the respective data 126 and 128 to ensure that timestamps specified in the command data 128 are aligned with the correct points in the media data 126 so that operations specified in the command data 128 are performed at the correct time. For example, the editor may ensure that the visual and auditory cues in the media data 126 are time synchronized with the operations in the command data 128. This time synchronization may account for inherent latency in the systems employed by users 112 to playback the media data 126 (e.g., output latency involved in casting media content to a peripheral display system, latency in wireless data transmission from the computing device 110 to a nearby fitness apparatus 120, etc.).

As depicted in FIG. 1, the instructor's 106 computing device 102 can send the media data 126 and the command data 128 to the remote system 108. The client application 136 of the computing device 102 may encode the media data 126 and/or the command data 128 before sending encoded media data 126 and/or command data 128 to the remote system 108, and/or before storing encoded media data 126 and/or command data 128 in the memory 132 of the computing device 102. The remote system 108 may receive and store the media data 126 (e.g., a video file(s)) and the command data 128 (e.g., a JSON file(s)) in a data store 146 for on-demand access by one or more computing devices 110. In some embodiments, the data store 146 may maintain different versions of the same file of media data 126, such as a low-resolution version, a high-resolution version, a high definition (HD) version, a 4K version, and so on. This may allow for users 112 to download an appropriate version of the media data 126 based on the capabilities of the client systems on which the media data 126 is to be replayed. In some embodiments, the remote system 108 may act as a pass through, or relay server, that forwards or relays the media data 126 and/or the command data 128 in real-time for live streaming implementations where a user(s) 112 follows along with a live stream of an instructor 106 who is conducting a workout session at the same time as the user(s) 112 are following along. The remote system 108 may, in some instances be part of a network-accessible computing platform that is maintained and accessible via the computer network 114. Network-accessible computing platforms such as this may be referred to using terms such as "on-demand computing", "software as a service (SaaS)", "platform computing", "network-accessible platform", "cloud services", "data centers", and so forth.

As further depicted in FIG. 1, a computing device 110(1) of a user 112(1) may receive the media data 126 and the command data 128 over the network 114 from the remote system 108. The computing device 110(1) may represent a personal computing device, such as a tablet computer, although the computing device 110(1) is not limited to a configuration of a tablet That is, the computing device 110(1) can be implemented as any suitable type of computing device including, without limitation, a PC, a desktop computer, a laptop computer, a mobile phone (e.g., a smart phone), a tablet computer, a portable digital assistant (PDA), a wearable computer, a set-top-box (STB), a game console, a smart television, and/or any similar computing device 110. In accordance with various embodiments described herein, the terms "computing device," "personal computing device," "personal computer," "computer," "mobile device," "wireless device," "communication device," "wireless communication device," "wireless terminal," "mobile terminal," "user device," "user equipment (UE)," "client device," "client computing device," "computer display device," and "device," may be used interchangeably herein to describe any computing device 110 that is capable of executing applications, playing back the media data 126, processing the command data 128 (described in more detail below), and communicating with (e.g., send/receive data to/from) other devices, such as a nearby fitness apparatus 120 and/or the remote system 108.

The computing device 110(1) is shown as including one or more processors 148, memory 150 (or non-transitory computer-readable media 150), and a communications interface(s) 152. These components may be implemented similarly to the processor(s) 130, memory 132, and communication interface(s) 134 described with reference to the computing device 102, and, as such, details of these components will not be explained again for the sake of brevity, as the description of the processor(s) 130, memory 132, and communication interface(s) 134 may be referenced herein to understand example implementations of the processor(s) 148, memory 150, and communication interface(s) 152. It is also to be appreciated that the computing devices 110(2) and 110(3) may include the same or similar components as shown and described with reference to the computing device 110(1) of FIG. 1, and that the computing devices 110 may, in some embodiments, be integrated into their respective fitness apparatuses 120 such that data is merely sent from the computing device 110 over a wire to a processor(s) of the fitness apparatus 120 to control aspects of the output provided by the fitness apparatus 120.

The computing device 110(1) is shown as having a client application 154 installed in the memory 150. The client application 154 may represent an executable application (e.g., code, computer-executable instructions, etc.) that is configured to decode the media data 126 and/or command data 128, to playback the media data 126 received from the remote system 108, to process the command data 128 received from to the remote system 108, to generate and send commands to the fitness apparatus 120(1) based at least in part on the command data 128, and/or to cause presentation of graphical overlays atop media content based at least in part on the command data 128. The client application 154 may provide a user interface for the user 112(1) to initiate playback of the media data 126 (e.g., a video file(s)) representing a workout session conducted by an instructor 106. The user 112(1) can provide user input (e.g., select a button, such as a physical button on the device 110(1) or a soft button (e.g., a "play" icon) on a touch screen), issue a voice command, etc.) to start playback of the media data 126 or to start the workout session when the user 112(1) is ready to start.

When playback of the media data 126 occurs on the device 110(1), media content corresponding to the media data 126 may be output on an output device. This media content may show a video of the instructor 106 conducting a workout session (e.g., demonstrating exercise movements over the duration of the session, parts of the session, etc.) and may include audio of the instructor 106 uttering verbal instructions/directions and/or recommendations/tips over the duration of the session, or parts of the session. A "workout session," in this sense, may comprise multiple exercise movements (e.g., a series of exercise movements), which may be performed in a particular sequence over the duration of the workout session. The output device may be a display 156 and/or a speaker(s) of the computing device 110(1) itself. In some embodiments, the user 112(1) may optionally provide user input to the computing device 110(1) that causes the device 110(1) to cast the media content to a peripheral system 158, such as a peripheral display system, during playback of the media data 126. Such a peripheral system 158 may be a television in the user's 112(1) environment 118 (e.g., a living room television) that includes a larger display than the display 156 of the computing device 110(1). This may improve the user experience if the display 156 of the computing device 110(1) is relatively small, if the computing device 110(1) is not easily propped up in a position where the user 112(1) can view the display 156, and/or in a group setting with multiple users 112 in the environment 118. In some embodiments, the computing device 110(1) may represent a mobile phone that the user 112(1) can carry in a pocket or a similar holster, placed on a nearby table, on a dedicated stand, etc., which may be convenient for the user 112(1) to provide user input during the workout session. In other embodiments, the computing device 110(1) may be a wearable device that is conveniently situated on the user's 112(1) body.

Starting the playback of the media data 126 via the client application 154 may also cause the client application 154 to access and begin processing the command data 128 (e.g., a JSON file(s)). Processing the command data 128 enables the client application 154 to determine what operations to perform, and at what time (relative to the playback of the media data 126) to perform those operations. A user profile 160 of the user 112(1) may be stored in the local memory 150 of the computing device 110(1) and/or at the remote system 108 for access by the computing device 110(1). The user profile 160 may specify user data that is personal to the user 112(1), such as information about the user 112(1) (e.g., his/her name, contact info, height, weight, fitness condition, etc.), which may include a history of output parameters for the fitness apparatus 120(1) associated with previous workout sessions involving the user 112(1). For example, the user profile 160 may specify a sequence of intensity values at which output was provided by the fitness apparatus 120(1) over a duration of a previous workout session performed by the user 112(1) at a time in the past. For example, in a previous workout session, the user 112(1) may have started the session at time $t_1$ with an overall electrical impulse intensity of 60 (again, "60" represents an arbitrary unit of measurement), followed by an increase to an intensity of 70 at time $t_2$, followed by an increase to an intensity of 75 at a subsequent time, and so on and so forth. The resulting sequence of intensity values may be saved in the user profile 160 of the user 112(1), and this sequence of intensity values may represent an intensity profile of the user 112(1), similar to the intensity profile of the instructor 106. It is to be appreciated that the user profile 160 can maintain multiple intensity profiles that correspond to multiple past workout sessions conducted by the user 112(1). In addition, there may be multiple sets of parameters and settings in the user profile 160 for different training modalities or types.

The user 112(1) may provide credentials (e.g., username, password, biometric data, etc.) to log into the client application 154 so that the client application 154 can access the user profile 160 of the user 112(1). At the start of a workout session, the client application 154 may access the user profile 160 of the user 112(1) to determine a starting intensity value at which the output is to be provided by the fitness apparatus 120(1) so that the intensity profile is customized to the user 112(1) by providing output via the fitness apparatus 120(1) at an appropriate intensity level. The starting intensity value may be based on a starting intensity value of a past (e.g., a previous) workout session, as indicated in the user profile 160, or a default starting intensity if there is no history on the user 112(1). Initially, the user 112(1) may navigate to a setup menu of the client application 154 to enter information such as body type, experience level, fitness condition, etc., which may be used by the client application 154 to select an appropriate starting intensity of output provided by the fitness apparatus 120(1).

As the playback of the media data 126 ensues on the device 110(1), and as the client application 154 processes the command data 128 in parallel, the client application 154 can monitor the playback of the media data 126 to determine when the playback has reached a timestamp specified in the command data 128. For example, the command data 128 may specify that a set of one or more operations are to be performed when a first timestamp is reached during playback of the media data 126. A first operation, of the set of operations, may comprise sending a command to the fitness apparatus 120(1) to control an aspect of output provided by the fitness apparatus 120(1). In embodiments where the fitness apparatus 120(1) represents an EMS suit worn by the user 112(1), the command may correspond to controlling an aspect of an electrical impulse(s) delivered via an electrode(s) of the EMS suit, such as by controlling the initiation, cessation, or adjustment of an intensity of the electrical impulse(s), and/or other settings or changes. This allows for the fitness apparatus 120(1) to provide output that is synchronized with the media content the user 112(1) is seeing and/or hearing on the output device (e.g., the peripheral system 158) in the environment 118. For instance, the instructor 106 exhibited in the media content may utter the verbal instructions "OK, let's do a squat in 3, 2, 1, go!", and at a time when the instructor 106 says the word "go", the EMS suit worn by the user 112(1) may deliver an electrical impulse to a muscle group(s) (e.g., the user's 112(1) legs, arms, chest, abdominals, and/or back) to elicit muscle contraction at a time when the instructor 106 says the word "go" (i.e., in synchronization with a particular verbal instruction and/or visual demonstration exhibited in the media content). This synchronization is achieved by having the operations specified in the command data 128 driven by the timestamps in the media data 126; or, slaving the operations to the timestamps within the media data 126, with high precision. Latency of sending wireless commands to the fitness apparatus 120(1) may be accounted for, such as by having the device 110(1) send a command slightly before the point in the media content when the muscle contraction should start. In any case, the media data 126 can provide the pace instead of a clock of the computing device 110 the client application 154 is executing on. The duration of the impulses provided by an EMS suit 320 of the user 112(1) may correspond to the durations experienced by the instructor 106 (e.g., an impulse for a duration of 4 seconds followed by a 4-second rest period). Other operations, of the set of operations specified in the command data 128 in association with the first timestamp, may relate to causing graphical overlays to be presented atop the media content at an appropriate time (e.g., by presenting graphic information pertaining to the name of the current exercise movement, the time remaining until an impulse or until a rest period, whether a pulse is currently on or off, etc.).

In addition to being time synchronized with the media content, the output provided by the fitness apparatus 120 may be provided in accordance with a customized intensity profile for the user 112 that is commensurate or proportional with an intensity profile of the instructor 106 in terms of the timing and durations of fitness apparatus 120 output. For example, the intensities of the impulses provided by the EMS suit 320 of the user 112 over the duration of the workout session may be extrapolated from the intensity profile associated with the instructor 106, which is exhibited in the command data 128. That is, if the instructor 106 started at an overall intensity of 90 and increases the intensity to a value of 120 thereafter, and if the user started at an overall intensity of 60, the intensity of the impulses delivered via the EMS suit 320 of the user 112(1) may be extrapolated to an intensity value of 80 at the time when the intensity value of 120 delivered via the EMS suit 220 of the instructor 106, as exhibited in the media content.

To initiate an electrical impulse, the client application 154 may wirelessly send a command to the EMS suit 320 worn by the user 112(1), and a controller (e.g., impulse pack 300) of the EMS suit 320 may receive and process the command to deliver a corresponding electrical impulse via one or more electrodes of the EMS suit 320 (e.g., electrodes that are positioned on the user's 112(1) chest to elicit muscle contraction of the pectoral muscles). During an electrical impulse, the user 112(1) may mimic the exercise movement (e.g., a squat, a lunge, an upright shoulder press, a punching motion, a kicking motion, etc.) demonstrated by the instructor 106, as exhibited in the media content, thereby going through the same motions the instructor 106 is demonstrating. The user 112(1) may also follow the instructor's 106 verbal directions/instructions explaining each exercise movement, announcing the start of the impulse to help the user 112(1) flex his/her muscles in time for the correct execution of the exercise movement, counting down the number of repetitions, as well as motivating the user 112(1).

Furthermore, the computing device 110(1) may provide a user interface for the user 112(1) to adjust the intensity of the output provided by the fitness apparatus 120(1) at one or more times during the workout session. This user interface can be provided in any suitable manner, such as a VUI, a GUI, etc. FIG. 1 shows the client application 154 as presenting, on the display 156, a first selectable element 162 (e.g., a "plus" icon) and a second selectable element 164 (e.g., a "minus" icon). The first selectable element 162, upon selection, may cause the device 110(1) to send a command to the fitness apparatus 120(1) to increase a current intensity level at which the output is provided by the fitness apparatus 120(1) to an increased intensity level, and the second selectable element 164, upon selection, may cause the device 110(1) to send a command to the fitness apparatus 120(1) to decrease a current intensity level at which the output is provided by the fitness apparatus 120(1) to a decreased intensity level. As such, if the user 112(1) feels like the intensity of the output provided by the fitness apparatus 120(1) is too much, the user 112(1) can provide user input to the computing device 110(1) (e.g., by selecting the second selectable element 164) to decrease the output provided by the fitness apparatus 120(1) at any time that the user 112(1) desires to do so. Conversely, if the user 112(1) feels like the intensity of the output provided by the fitness apparatus 120(1) is not enough, the user 112(1) can provide user input to the computing device 110(1) (e.g., by selecting the first selectable element 162) to increase the output provided by the fitness apparatus 120(1) at any time that the user 112(1) desires to do so. This user input can be recorded by the client application 154 as part of the user's 112(1) intensity profile for the workout session, and maintained in a history of intensity profiles of the user 112(1).

It is to be appreciated that the selectable elements 162 and 164 may provide an easy-to-use interface for the user 112 to adjust intensity of the output provided by the fitness apparatus 120 between a minimum and a maximum intensity. Accordingly, a visual indicator (e.g., a slider bar, dial, etc.) may also be presented on the display 156 in response to the user 112 providing user input to one of the selectable elements 162 and/or 164 in order to indicate to the user 112 where the current intensity level is set between the minimum and the maximum settings. These settings can be translated by the client application 154 to actual values that pertain to the output parameter settings of the fitness apparatus 120, without the user 112 having to be concerned with what the actual value is.

Furthermore, the adjustments to the output intensity made by the user 112 may be adjustments for an overall intensity, while a fitness apparatus 120 may provide outputs at a more granular level. For example, with an EMS suit 320, there may be multiple electrodes (e.g., an array of electrodes) corresponding to multiple muscle groups designated by respective channels of an array of channels. For example, a first channel may be designated for the legs, a second channel for the abdominals, a third channel for the back, a fourth channel for the chest, a fifth channel for the arms, and so on and so forth. The electrical impulse intensity for these respective channels may be adjustable independent of the other channels, and each channel may be independently operated (e.g., electrical impulses may be delivered via electrodes positioned on the legs of the user, without eliciting muscle contraction of the user's upper body at all). Therefore, muscle groups can be isolated to contract particular targeted muscles, and the intensities of each channel may be set at relative levels (e.g., less intense on the legs, more intense on the arms, etc.). Thus, the client application 154 can maintain the relative, per-channel (or per-muscle group) settings of intensity levels, and the adjustments made by the user 112 may increase or decrease the overall intensity (e.g., increase or decrease all channels simultaneously) while the relative, per-channel intensities are maintained. It is to be appreciated that, in some embodiments, the client application 154 may provide a user interface to allow the user 112 to adjust intensities on a per-channel basis (e.g., increase or decrease the legs without adjusting the intensity of the output on the other muscle groups). It is also to be appreciated that the client application 136 executing on the instructor's 106 device 102 may be configured to operate similarly to this description of the user's 112 device 110.

The client application 154 may be configured to track user adjustments made during a workout session so that user behavior is collected over time (e.g., over multiple sessions), and this user behavior data may be used, accessed, and/or referenced to customize future workout sessions. For example, if a user 112 performed well during a given workout session (e.g., the user 112 increased the intensity to end up at a higher intensity level than the user 112 was projected to end up at), then the starting intensity for a next workout session of the user 112 may be adjusted to a higher value corresponding to the user's intensity adjustments in the previous workout session.

In some embodiments, the client application 154 may be configured to pair with, and receive data from, peripheral devices, such as wearables (e.g., a heart rate monitor, a smart watch, a fitness band, etc.) to determine attributes and other existing conditions of a user 112, which may factor into starting intensities of fitness apparatus 120 output and/or real-time adjustments to the fitness apparatus 120 output during a workout session. The client application 154 may additionally, or alternatively, access other data sources over the network 114, such as to determine the current temperature and/or weather at the geographical location of the user 112 (e.g., if the weather is particularly hot, the intensity of the workout session may be adjusted downward so as to not overstress the user 112 in such hot conditions), etc. As another example, if a heart rate monitor indicates that the user 112 is exceeding a recommended heart rate, the intensity of fitness apparatus 120 output can be decreased in real-time during the session. If a fitness tracker worn by the user 112 indicates that the user 112 did not sleep well the night before, and/or that the user 112 took an abnormally high number of steps the day before a workout session, the client application 154 may take this information into account in setting the starting intensity value of the fitness apparatus 120 output. At least some of this information can also be displayed as a graphical overlay atop the media content during a workout session (e.g., displaying graphical overlays indicating the user's 112 current heart rate, the current weather, etc.).

As depicted in FIG. 1, a group of devices 110 may be collocated in the environment 118, and users 112 of the collocated devices 110 may be using their own fitness apparatuses 120, respectively. For example, a second user 112(2) of the second computing device 110(2) may be using a second fitness apparatus 120(2) (e.g., an EMS suit 320), and a third user 112(3) of the third computing device 110(3) may be using a third fitness apparatus 120(3) (e.g., an EMS suit 320), and these users 112, devices 110, and fitness apparatuses 120 may be collocated in the environment 118 with the first device 110(1) and the first user 112(1) who is using the first fitness apparatus 120(1). The client application 154 may provide an interface (e.g., a VUI, GUI, etc.) for the user 112(1) to create a group of devices 110, where one device 110 acts as a master device, and the remaining devices 110 act as slave devices for purposes of synchronizing the output provided by the fitness apparatuses 120 with the media content that is being consumed by the users 112 in the environment 118. The devices 110 may be formed into a group using any suitable techniques for designating a master device (e.g., at request of a user 112, by conducting a throughput test to determine which device 110 is in the best position to transmit data to other devices 110 in the environment 118, etc.). The devices 110 may be connected over a local area network (LAN) (e.g., a WiFi router or a similar access point) to pass data back and forth between devices 110.

If the first device 110(1) is designated as the master device in the group, the first device 110(1) may initiate playback of the media data 126, and may iteratively send timestamp data to the slave device(s) 110 in the group, which indicates, to the slave device(s) 110, a current timestamp reached during the playback of the media data 126 on the master device 110(1). Any suitable technique for data exchange can be used to send timestamp data from the master device 110(1) to one or more slave devices 110(2), 110(3), etc. in a group, such as user datagram protocol (UDP) broadcast techniques where packets are transmitted at relatively short time intervals, or any other protocol or technique to send data over a wireless LAN (WLAN). Each device 110 in the group may download the command data 128 independently so that the command data 128 is processed on the respective devices 110 while the media data 126 is played back on the master device 110(1). As mentioned, the master device 110(1) may cast media content to a peripheral system 158 for output thereon, which may be desired in a group setting where a larger screen can be viewed by multiple users 112 in the environment 118. In some embodiments, the master device 110(1) may send the command data 128 to the slave devices 110(2), 110(3), etc., thereby acting as a hub for distribution of the command data 128 to the other devices 110 in the group. By designating one device 110(1) as a master device that keeps track of the playback of the media data 126 and informs the other devices 110 (slave devices) of the progress of the playback (e.g., by iteratively sending timestamp data to the slave devices), the group can synchronize the output of the fitness apparatuses 120 in the environment 118 with the media content by sending commands to the fitness apparatuses 120 based on the command data 128, which is driven by the playback of the media data 126 on the master device 110(1).

FIG. 2 illustrates an instructor 106 who is in the process of recording a workout session while using an EMS suit 220, which is an example of a fitness apparatus 120(4) usable by the instructor 106. A recording device 104 (e.g., a video camera) is used to generate media data 126 of the workout session (e.g., a video file(s)), while a nearby computing device 102 is used to generate command data 128 for controlling an EMS suit 320 of a user 112 who will access the command data 128 after its creation. The instructor 106 is shown in an environment 116 (e.g., a studio production environment) where a recording device(s) 104 is setup. In this example, the recording device(s) 104 includes a video camera 122 and a built-in and/or external microphone 124, which is used to record the workout session to generate the media data 126, such as in the form of a video file(s). The computing device 102 is also used during the workout session to (wirelessly) send commands to the EMS suit 220 for initiating, ceasing, or adjusting the intensity of electrical impulses delivered via the EMS suit 220. This may be in accordance with a predetermined sequence of output parameters for the workout session (e.g., 4-second impulses, followed by 4-second rest periods, for a defined number of repetitions per exercise movement, etc.). FIG. 2 shows that the EMS suit 220 includes an impulse pack 200, which may include a wireless receiver (e.g., a Bluetooth radio) to receive the commands from the computing device 102, and a processor(s) to process the received commands for delivering electrical impulses via the appropriate electrodes of the EMS suit 220. The computing device 102 may be mounted on a stand 202 so that the instructor 106 does not have to hold the computing device 102 during the workout session, and so that the instructor 106 may conveniently provide user input by quickly touching a control (e.g., a selectable element 142, 144) presented on the display 140 of the computing device 102 during the workout session. Additionally, or alternatively, the computing device 102 may provide a VUI for the instructor 106 to issue voice commands to adjust the intensity (e.g., overall intensity) of the electrical impulses delivered via the EMS suit 220. The sequence of commands sent to the EMS suit 220 over the duration of the workout session (including those that are based on the user input provided by the instructor 106 to adjust the intensity of the electrical impulses) are used to generate the command data 128 that specifies the operations and the timestamps within the media data 126 at which the operations are to be performed during playback of the media data 126, such as when a computing device 110 of a user 112 initiates playback of the media data 126 thereon and processes the command data 128 in parallel with the playback.

The instructor 106 may follow a script 204 of the workout session, which may have been written in advance, and which may be output on a teleprompter 206 in the environment 116 while the instructor 106 is conducting the workout session wearing/using the EMS suit 220. Pre-scripting the workout session in this manner allows the instructor 106 to deliver lines (e.g., verbal directions) on cue, and to demonstrate exercise movements pursuant to the script, much like an actor follows a movie script. The client application 136 may have access to an electronic version of the script and may be casting content of the script 204 to the teleprompter 206 for output of the script 204 thereon. The teleprompter 206 may be outside of the field of view of the camera 122 of the recording device 104 so that it is not visible in the resulting media content. Following a script 204 in this manner also allows the instructor 106 to live stream a workout session while computing devices 110 of users 112 process command data 128 that has been generated in accordance with the same script 204. An example script 204 of a workout session may begin with a welcome segment where the instructor 106 welcomes users 112 who may be consuming the media content that the instructor 106 is recording, either in real-time or on-demand at a later time. The script 204 may inform the instructor 106 of the names of the exercise movements in the session and the sequence of the exercise movements, as well as the number of repetitions of each exercise movement, etc. After the welcome segment, the script 204 may inform the instructor 106 of what to say during each exercise repetition and when to say it. For example, at the beginning of the session, the script 204 may prompt the instructor 106 to say "OK, here we go, the first exercise for today is X, and we are going to do 8 reps (4 seconds on, 4 seconds off) . . . and here we go, let's start!" There may be a warmup phase prior to a full-intensity exercise phase of the session. The script 204 may conclude with a goodbye segment where the script 204 includes tips and reminders that the instructor 106 says aloud, such as "remember to hydrate well and take some magnesium," and/or "tomorrow is strength training, remember to go for a run," etc.

Different scripts 204 may be used for different experience levels for a given workout session. For example, a script 204 for a Level 1 class (e.g., an introductory class) may have more lines for the instructor 106 to deliver, such as tips, warnings, and reminders for beginners who may need more assistance from the instructor 106. A script 204 for a Level 2 class (e.g., an intermediate class) may have fewer lines for the instructor 106 to deliver so that the users 112 who have some experience are not annoyed by too many instructions, while the instructor 106 still communicates common mistakes (e.g., "OK, make sure your left knee doesn't go in . . . and go!"). Meanwhile, a script 204 for a Level 3 class (e.g., an expert class) may have even fewer lines for the instructor 106 to deliver, and/or the script 204 may include extra educational information that the instructor 106 can deliver verbally during the workout session, which may be of interest to the expert users (e.g., "for this exercise, we are targeting muscle groups X, Y, and Z").

FIG. 3 illustrates a user 112 who is using an EMS suit 320 (which is an example of a fitness apparatus 120) being controlled in synchronization with media content 302 output via an output device, such as a peripheral system 158 that includes a display and/or a speaker(s). As shown in FIG. 3, the user 112 may be in an environment 118 and using an EMS suit 320. The user 112 may place his/her computing device 110 on a stand 304 so that it is easily accessible to the user 112 during the workout session, and so that the user 112 does not have to hold the device 110 to provide user input thereto. The device 110 is playing back media data 126 corresponding to media content 302 featuring an instructor 106 conducting a workout session. In the example of FIG. 3, the device 110 is casting the media content 302 to the peripheral system 158, which may include speakers to output audio content, and a display to output image content. In this example, the peripheral system 158 is a living room television, and the environment 118 is the user's 112 living room. It is to be appreciated that the media content may comprise video content and audio content, and that the video content may be output on a first output device (e.g., the display of the peripheral system 158) while the audio content is being output via a second output device (e.g., a speaker(s) of the device 110), or vice versa. The device 110 in FIG. 3 is also processing command data 128, as described herein, to transmit commands to the EMS suit 320 at appropriate times so that the user 112 feels electrical impulses at the proper times (e.g., when the instructor 106 issues a verbal command to begin an exercise movement and/or begins demonstrating the exercise movement, the user 112 may feel a muscle contraction).

Figure 4:
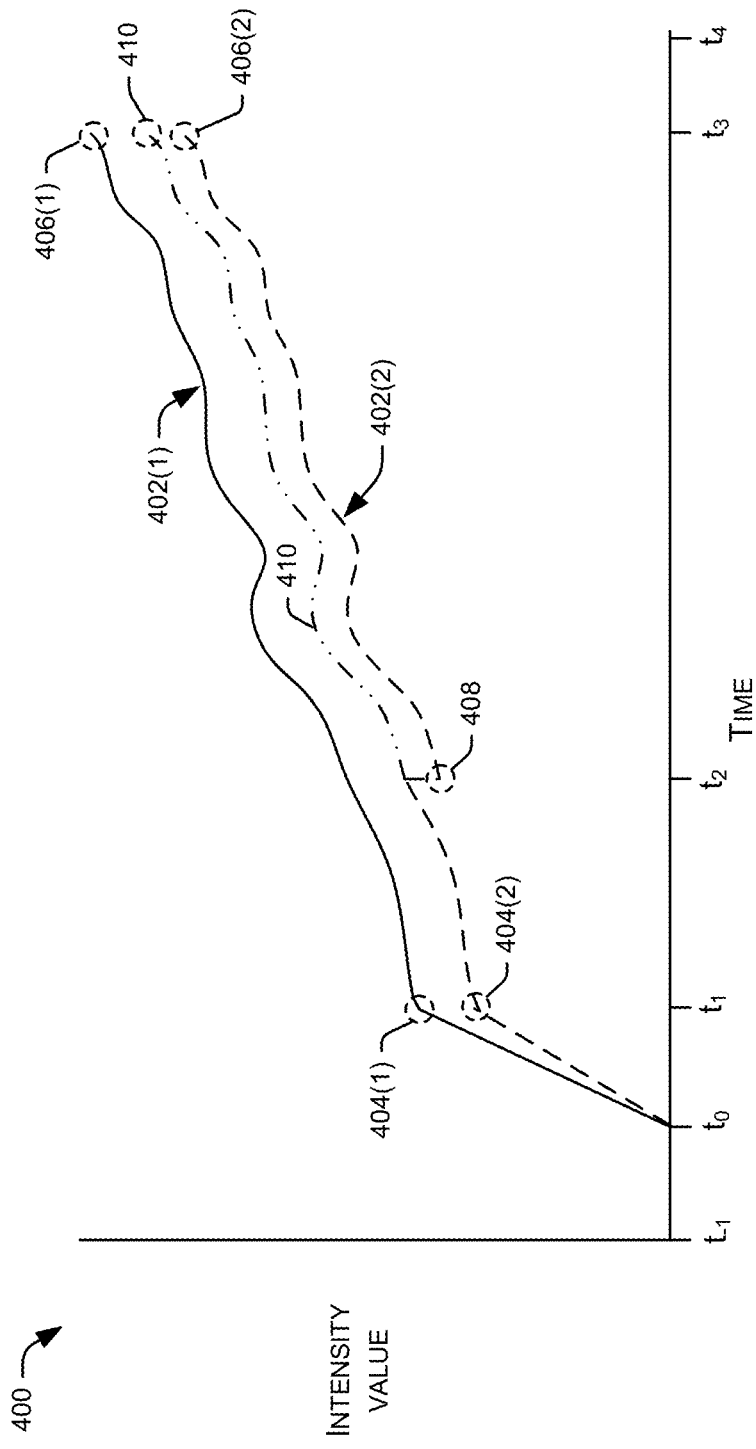
FIG. 4 illustrates a graph showing intensity profiles associated with a workout session.

FIG. 4 illustrates a graph 400 showing intensity profiles 402 associated with a workout session. That is, the graph 400 shows sequences of intensity values plotted over time for individual users who have conducted a workout session. These intensity profiles 402 provide a visual aid to understand how the output of a fitness apparatus 120 may be controlled over a duration of the workout session. In embodiments where the fitness apparatus 120 is an EMS suit 220/320, the intensity values may correspond to an overall intensity level of electrical impulses delivered via the EMS suit 220/320 at any given time.

The first intensity profile 402(1) (also denoted by the solid plot line in the graph 400) may represent an intensity profile of the instructor 106 who conducted a workout session. The time period from time, $t_{-1}$, to time, $t_0$, may represent a welcome segment of a workout session. During this welcome segment, the instructor 106 may welcome users 112 to the workout session by providing introductory comments and information regarding the upcoming workout session, such as the exercise movements involved, targeted muscle groups, the type of fitness goals that is to be achieved, the duration of the workout session, etc. The time period from time, $t_0$, to time, $t_1$, may represent a start of an exercise portion where the fitness apparatus 120(4) starts to provide output. In some embodiments, this time period may represent a warm-up phase of the workout session (e.g., a two-minute warm up). During this time period, the output of the fitness apparatus 120(4) may ramp (e.g., linearly) from an intensity value of zero to a starting intensity value 404(1). For example, the starting intensity value 404(1) may be determined from a previous workout session specified in the user profile 138 of the instructor 106. If there is no workout history on the instructor 106, the starting intensity value 404(1) may be based on a default intensity value, which may be based on information provided by the instructor 106 in advance, such as experience level, body type, fitness condition, etc. For an EMS suit 220, this starting intensity value 404(1) may represent an increase in electrical impulse intensity (e.g., by ramping the amount of current, voltage, etc.). For example, 48 seconds into the workout session, the impulses may start with parameters X (X representing one or more parameters such as a starting intensity 404(1) of the electrical impulse, duration of the impulse, etc.). It is to be appreciated that the starting intensity value 404(1) may represent an overall intensity of the fitness apparatus 120(4), while the fitness apparatus 120(4) may be configured to provide output via multiple channels at relative intensity offsets. Thus, the user profile 138 of the instructor 106 may indicate multiple starting intensity values for multiple channels of output (e.g., multiple electrodes of an EMS suit 220), which can be represented by the single starting intensity value 404(1) in the graph 400.

The time period from time, $t_1$, to time, $t_3$, on the instructor's 106 intensity profile 402(1) may represent a period of time where output provided by the fitness apparatus 120(4) progressively increases over the duration of the workout session to an ending intensity value 406(1) at the end of the exercise portion of the session. In some embodiments, this time period may represent a full body strength training (e.g., 15 minutes), followed by an abs and core training (e.g., 5 minutes), etc. For example, 150 seconds into the workout, intensity of the output provided by the fitness apparatus 120(4) may increase by 1% overall during a full-body strength training portion, and so on and so forth. The time period from time, $t_3$, to time, $t_4$, may represent a goodbye segment of the workout session where the instructor 106 is providing reminders and other tips for the users 112, as well as thanking the users 112 for participating in the workout session. In some embodiments, this may include, or be preceded by, a cool down phase of the workout session. The intensity profile 402(1) associated with the instructor 106 may represent intensity adjustments for the output of the fitness apparatus 120(4) that include both the pre-programmed sequence of output parameters described herein (e.g., pre-programmed 4-second impulses followed by 4-second rest periods), as well as the manual adjustments made by the instructor 106 during the workout session. In some embodiments, the instructor 106 may add small breaks to the workout to allow for hydration or a change of position from standing to a ground-based set of exercises. This way, the user 112 can benefit from all the adjustments and instructions given as if the instructor 106 would operate his EMS suit. In some embodiments, the instructor 106 can change the impulse parameters to include different training modalities in one session. For example, the sessions could start with 2 minutes of warmup, followed by 15 minutes of explosive strength training, followed by 5 minutes focusing on the core of the body with an endurance modality, and finishing with 3 minutes of a relaxing cooldown. A total duration of the exercise portion of the session may be about 20 minutes, 30 minutes, 1 hour, etc., which may depend on the objectives, fitness goals, experience of the audience (e.g., users 112), etc.

The second intensity profile 402(2) (also denoted by the dashed plot line in the graph 400) may represent an intensity profile of a user 112. By plotting this intensity profile 402(2) on the same graph 400 as the instructor's 106 intensity profile 402(1), one can appreciate that intensity profiles 402 may be different for different users, even though the workout session is the same. During the time period from time, $t_0$, to time, $t_1$, the fitness apparatus 120 of the user 112 may start to provide output. During this time period, the output of the fitness apparatus 120 may ramp (e.g., linearly) from an intensity value of zero to a starting intensity value 404(2) that is specific to the user 112. For example, the starting intensity value 404(2) may be determined from a previous workout session specified in the user profile 160 of the user 112. If there is no history on the user 112, the starting intensity value 404(2) may be based on a default intensity value, which may be based on information provided by the user 112 in advance, such as experience level, body type, fitness condition, etc. In the example of FIG. 4, the user's 112 starting intensity value 404(2) is less than the instructor's 106 starting intensity value 404(1). For an EMS suit 320, this may mean that the user's 112 EMS suit 320 ramps up to an intensity level that is less than the intensity level experienced by the instructor 106 at the same time during a common workout session. It is to be appreciated that the starting intensity value 404(2) may represent an overall intensity of the fitness apparatus 120 of the user 112, while the fitness apparatus 120 may be configured to provide output via multiple channels at relative intensity offsets. Thus, the user profile 160 of the user 112 may indicate multiple starting intensity values for multiple channels of output (e.g., multiple electrodes of an EMS suit), which may be represented by the single starting intensity value 404(2) in the graph 400.

During the time period from time, $t_1$, to time, $t_2$, the user's 112 intensity profile 402(2) may track the corresponding portion of the instructor's 106 intensity profile 402(1), but the intensity values may be offset (e.g., a fraction of the intensity values associated with the instructor's intensity profile 404(1) during the same time period). For example, 49.565 seconds into the workout, when the instructor's 106 fitness apparatus 120(4) output intensity increases by 1% overall, the output of the user's 112 fitness apparatus 120 may increase by 1%, in synchronization with the instructor 106 announcing, in the media content 302, "OK, you're going to feel a little more muscle contraction in 3, 2, 1, now!" The 1% increase in the user's 112 intensity may correspond to a smaller degree of an increase than the 1% increase in the instructor's 106 intensity, assuming the instructor's 106 fitness apparatus is providing output at a higher overall intensity. In other words, if the instructor 106 were to announce a 1% increase in impulse intensity in the media content 302, the client application 154 may, based on the command data 128, send a command to the EMS suit 320 of the user 112 to implement this change at the correct time relative to the media content being output to the user 112. Notably, the user 112 does not have to make these adjustments, as they are encoded in the command data 128 and used to automatically control the fitness apparatus 120. Because the instructor's 106 intensity profile 402(1) may be exhibited in the command data 128, the sequence of intensity values for the user 112 can be extrapolated in advance to map out the user's 112 intensity profile 402(2), which will be followed unless and until the user 112 provides user input to adjust the intensity of the output provided by his/her fitness apparatus 120.

At time, t2, the intensity profile 402(2) of the user 112 decreases suddenly to a decreased intensity value 408. This may be caused by the user 112 providing user input in real-time during the workout session to decrease the intensity of the output provided by his/her fitness apparatus 120 (e.g., by selecting the second selectable element 164 on the display 156 of the computing device 110). The user 112 can adjust the intensity as desired to deviate from the pre-planned intensity profile 410 (also denoted by the dashed and dotted plot line in the graph 400) to create a customized intensity profile 402(2) that deviates from the pre-planned intensity profile 410. During the time period from time, $t_2$, to time, $t_3$, the output provided by the fitness apparatus 120 of the user 112 tracks the remainder of the instructor's 106 intensity profile 402(1) by progressively increasing over the duration of the workout session to an ending intensity value 406(2) at the end of the exercise portion, yet the intensity values plotted during this time period are lower to account for the user's 112 adjustment to the intensity level of the fitness apparatus 120 (e.g., decreasing the intensity to the decreased intensity value 408) earlier in the session. That is, the ending intensity value 406(2) may be different from a pre-planned ending intensity value 410 if the user 112 were to not provide any user input to adjust the intensity during the workout session.

Figure 5:
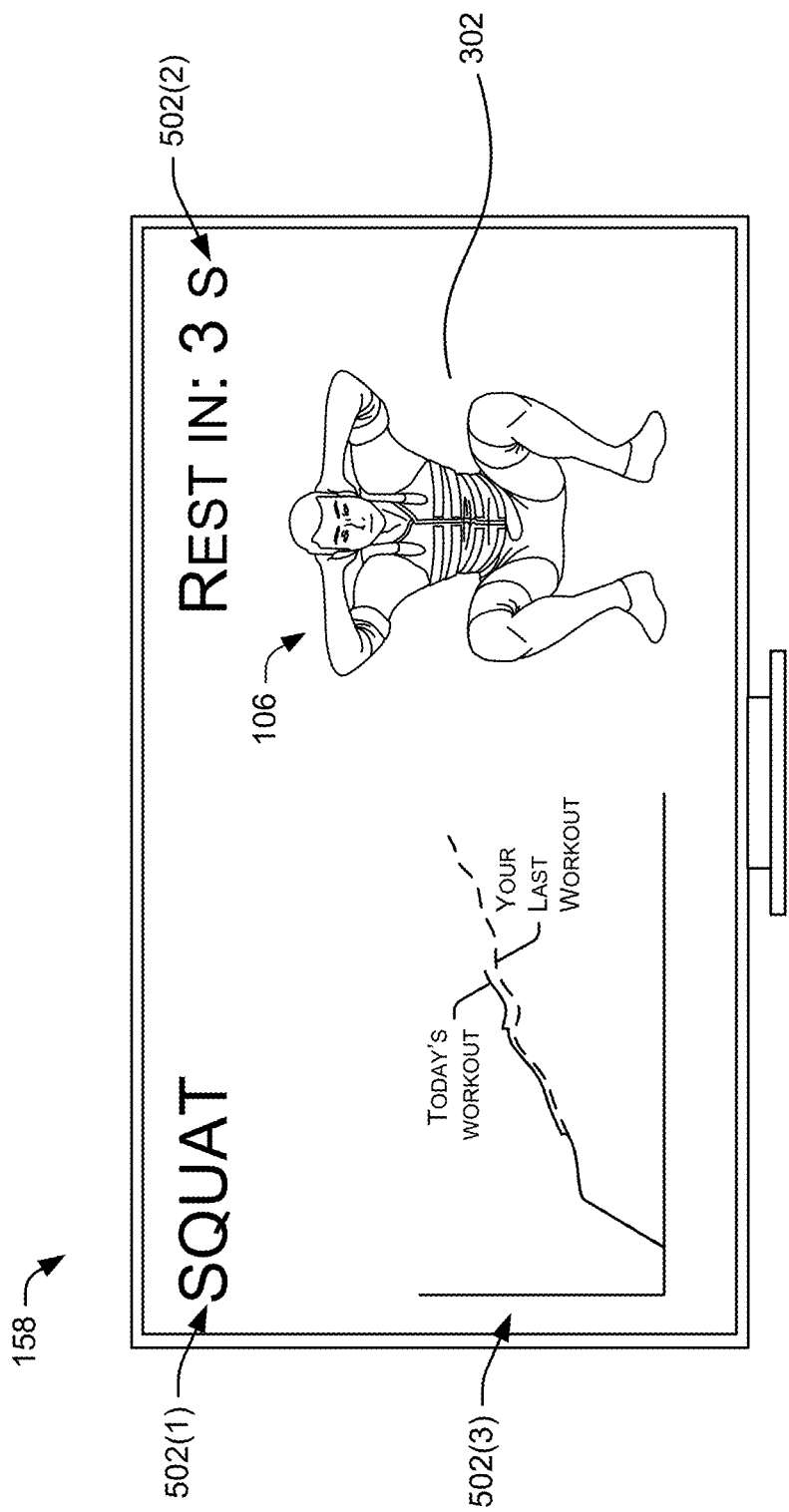
FIG. 5 illustrates examples of graphical information that can be overlaid atop media content in synchronization with the instructor's demonstrations and verbal instructions in the media content.

FIG. 5 illustrates examples of graphical information that can be overlaid on media content 302 in synchronization with the media content 302. FIG. 5 depicts the peripheral system 158 of FIG. 1 acting as the output device of the media content 302. The client application 154 executing on the computing device 110 may be casting the media content 302 to the peripheral system 158 in the example of FIG. 5 while processing the command data 128 and playing back the media data 126 in parallel. When the client application 154 determines that the playback of the media data 126 has reached a particular timestamp specified in the command data 128, the command data 128 may specify a display-related operation that is to be performed at that time during the playback of the media data 126. For example, when the playback reaches a particular timestamp, the device 110 may perform an operation that comprises causing presentation of graphical information 502 overlaying the media content 302 on the peripheral system 128 acting as the output device. Although the graphical information 502 is not shown as occluding portion of the media content 302 exhibiting the instructor 106 in the example of FIG. 5, the graphical information 502 is still considered to be overlaying the media content 302 in FIG. 5, and, in some scenarios, the graphical information 502 may very well occlude the portion of the media content 302 exhibiting the instructor 106. In these scenarios, the graphical information 502 may be presented as a semi-transparent overlay.

FIG. 5 shows an example where, at a particular time during the playback of the media data 126, the device 110 may cause presentation of first graphical information 502(1) that conveys the name of a current exercise movement (e.g., "Squat"). This first graphical information 502(1) may be overlaid atop the media content 302 in a portion of the display area (e.g., the upper left corner). At the same time during the playback of the media data 126, the device 110 may cause presentation of second graphical information 502(2) that conveys an amount of time remaining until a rest period when the output of the fitness apparatus 120 will cease to be provided. This second graphical information 502(2) may be overlaid atop the media content 302 in another portion of the display area (e.g., the upper right corner). It is to be appreciated that the client application 154 may have multi-language support to support multiple spoken languages. As such, if the user 112 specifies a spoken language in a settings menu (e.g., Spanish), then the graphical information 502 may be output in the appropriate language (e.g., Spanish). This may be enabled by the client application 154 having multiple language-specific graphical overlays corresponding to a particular operation, looking up the current language setting to determine the spoken language, and selecting the graphical overlay that is specific to that spoken language. FIG. 5 also shows third graphical information 502(3) that may be overlaid atop the media content 302 on the peripheral system 158 acting as the output device. This third graphical information 502(3) might convey the user's 112 progress and performance of the current workout session in the form of an intensity profile 402 plotted in real-time as a graphical overlay (e.g., "Today's Workout" in FIG. 5, denoted as the solid plot line). The third graphical information 502(3) may also convey a previous performance of the user 112 during a previous workout session in the form of an intensity profile 402 presented as a graphical overlay (e.g., "Your last workout" in FIG. 5, denoted as the dashed plot line). This allows the user 112 to compete against himself/herself during the current workout session (e.g., to improve since a previous workout). The example of FIG. 5 shows how the user 112 might be inspired to increase the intensity of the output provided by the fitness apparatus 120 in real-time, as described herein, in order to end up at a higher ending intensity value than a previous workout session.

It is to be appreciated that other social features can be implemented in a similar fashion for consenting users 112. For instance, instead of competing against one's self, multiple users 112 may compete against each other by having the client application 154 cause presentation of each user's progress and performance on the same graph to compare users' performance in a friendly competition. For instance, intensity profiles 402 of multiple users 112 collocated in the same environment 118, as shown in FIG. 1, or located in different geographical location but connected over the network 114, may be presented in the third graphical information 502(3) so that users 112 can compete against each other. As yet another example, the intensity profile of the instructor 106 may be presented in the third graphical information 502(3) so that the user 112 may compete against the instructor 106. The third graphical information 502(3) may be overlaid atop the media content 302 in another portion of the display area (e.g., the bottom left corner). In some implementations, this type of graphical information 502(3) may be presented throughout the duration of the workout session, or presented periodically (e.g., at particular timestamps during playback of the media data 126, at the request of the user 112 by providing user input to the device 110, etc.) as a check-in point so that the media content 302 is less occluded by graphical overlays.

The processes described herein are illustrated as a collection of blocks in a logical flow graph, which represent a sequence of operations that can be implemented in hardware, software, or a combination thereof. In the context of software, the blocks represent computer-executable instructions that, when executed by one or more processors, perform the recited operations. Generally, computer-executable instructions include routines, programs, objects, components, data structures, and the like that perform particular functions or implement particular abstract data types. The order in which the operations are described is not intended to be construed as a limitation, and any number of the described blocks can be combined in any order and/or in parallel to implement the processes.

Figure 6:
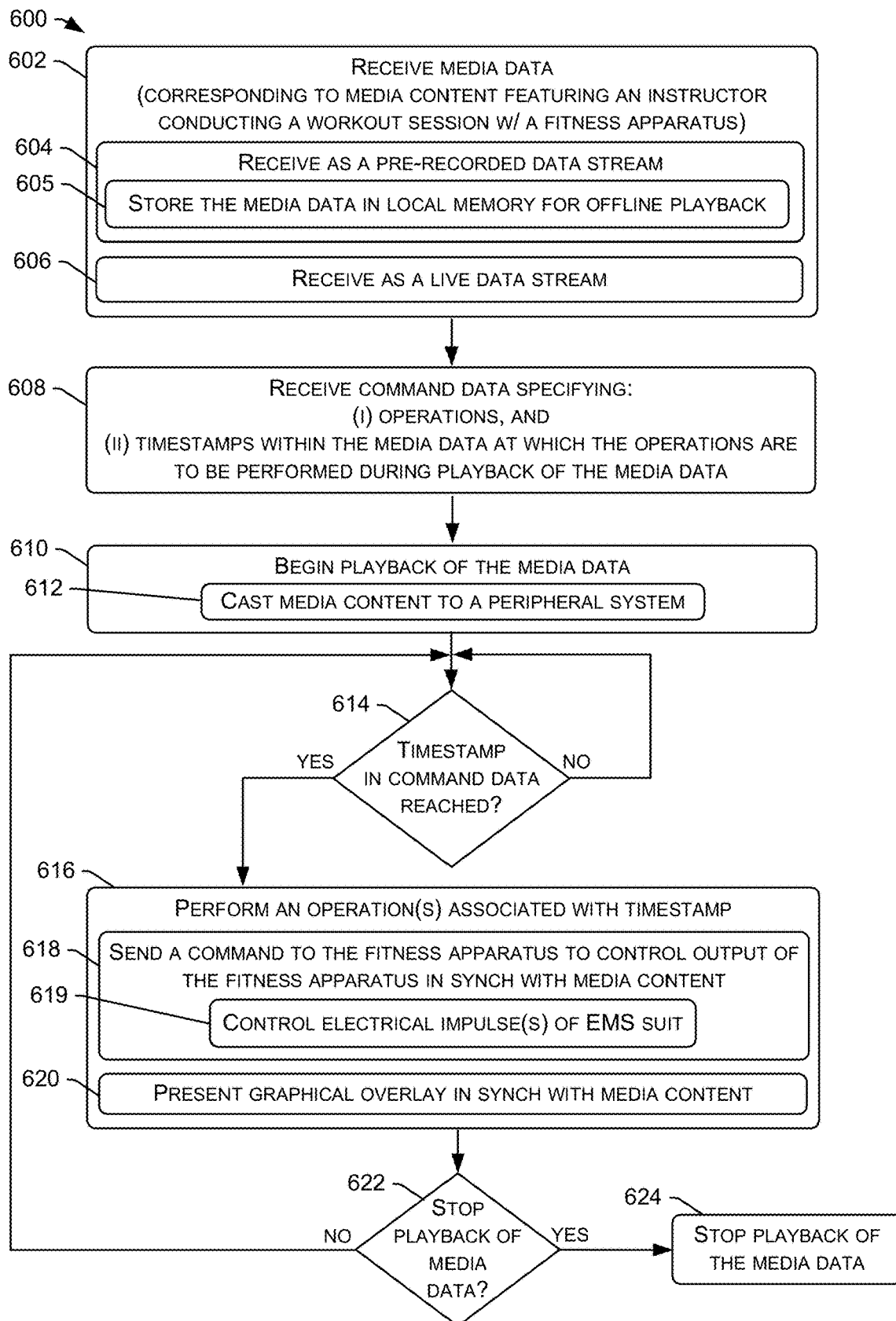
FIG. 6 is a flow diagram of an example process for controlling the output of a fitness apparatus in synchronization with media content.

FIG. 6 is a flow diagram of an example process 600 for controlling the output of a fitness apparatus in synchronization with media content. For discussion purposes, the process 600 is described with reference to the previous figures.

At 602, a device 110 of a user 112 may receive, over a network 114 from a remote system 108, media data 126 corresponding to media content 302 featuring an instructor 106 conducting a workout session. The media data 126 may comprise video data (e.g., image data and audio data), or the media data 126 may comprise audio data without image data, or image data without audio data. Furthermore, a client application 154 may be executing on the device 110 at block 602 and may execute instructions for receiving the media data 126 at block 602. As shown by sub-blocks 604 and 606, the media data 126 can be received in different ways, depending on whether the user 112 is accessing the media data 126 on-demand or as a live stream.

At sub-block 604, the device 110 may receive the media data 126 as a pre-recorded data stream. That is, the media data 126 may have been recorded at a time prior to receiving the media data 126 over the network 114 at block 602. In this case, the media data 126 may be received as a file(s), such as a video file(s), an image file(s), or an audio file(s). In some embodiments, the media data 126 may be streamed at sub-block 604 in the sense that it is played back on the device 110 as it is being received as a bitstream, where the device 110 may buffer the media data 126 until it is played back. As shown by sub-block 605, the device 110 may store the media data 126 in memory 150 of the device 110 (i.e., download the media data 126) so that the media data 126 can be played back, even if the device 110 is offline, or a network connection with the remote system 108 is otherwise slow. When the media data 126 is received as a pre-recorded data stream, timestamps may be encoded in the pre-recorded data stream, such as a video file, to denote different points within the media data 126 as the media data 126 is played back.

At sub-block 606, the device 110 may receive the media data 126 as a live data stream while the instructor 106 is conducting the workout session. Such a live data stream may include, without limitation, a video data stream corresponding to video content that represents the instructor 106 demonstrating exercises, as well as one or more audio data streams. At least one of the one or more audio data streams (e.g., a first audio data stream) may correspond to audio content that represents the instructor 106 issuing verbal directions for exercises. If there are multiple audio data streams, another audio data stream (e.g., a second audio data stream) may be used primarily, or exclusively, as an information stream that includes the timestamps (or time-based event data) associated with the media data 126. For instance, a "metronome" function may be provided via one of the available audio streams that is usable by the device 110 to determine the current timestamps within the media data 126, if the media data 126 is received as a live data stream. In some embodiments, the timestamps associated with the media data 126 are included in the video and/or audio data stream of the live data stream. That is, the timestamps may be included in the video data stream. Additionally, or alternatively, the timestamps may be included in the audio data stream (e.g., the first audio data stream) that corresponds to the audio content representing the instructor 106 issuing verbal directions for exercises. In this scenario, the audio data stream may include tones that are inaudible to the human ear (e.g., tones at frequencies outside of the frequency band that is audible to humans), or other markers or audio signatures that can be detected by the client application 154 of the device 110.

At 608, the device 110 may receive, over the network 114 from the remote system 108, command data 128 associated with the media data 126 received at block 602. The command data 128 may specify: (i) operations that are to be performed by the device 110, and (ii) timestamps within the media data 126 at which the operations are to be performed during playback of the media data 126 on the device 110. The command data 128 may be received before the media data 126 received, at the same time as the media data 126 is received, or after the media data 126 is received. The command data 128 may be received as a file(s), such as a JSON file, which may be executed on the device 110 using the client application 154 to determine which operations in the command data 128 are to be performed, and when they are to be performed during playback of the media data 126.

At 610, the device 110 may begin the playback the media data 126 for output of the media content 302 on an output device. The client application 154 may be utilized to playback the media data 126 at block 610. As mentioned, the device 110 may have downloaded the media data 126 at sub-block 605, in which case, the device 110 may access, from the memory 150, the media data 126 that was downloaded prior to beginning the playback the media data 126. The media content 302 may include video content (e.g., image content presented on a display and audio content output via a speaker(s)), audio content without image content (e.g., output via a speaker(s)), or image content without audio content (e.g., presented on a display(s)). The output device may include the display 156 and/or speaker(s) of the device 110. However, as shown by sub-block 612, the device 110 may cast the media content 302 to a peripheral system 158 (e.g., a system with a display and/or speakers), during the playback of the media data 126. The client application 154 may be used to cast the media content 302 to a peripheral system 158.

At 614, the device 110, via the client application 154, may determine whether the playback of the media data 126 has reached a particular timestamp of the timestamps specified in the command data 128 that is associated with an operation(s) to be performed. Accordingly, the device 110 may access the command data 128 it received at block 608 (e.g., by accessing the command data 128 from the memory 150) to make this determination at block 614, such as by identifying commands associated with particular timestamps, as specified in the command data 128. In an illustrative example, a first timestamp (at time, t=4 seconds) may be specified in the command data 128, and the client application 154 may monitor the status or progress of the playback of the media data 126 to determine whether the first timestamp has been reached at block 614. If the playback of the media data 126 has reached a timestamp that is not specified in the command data 128 as being associated with an operation to be performed, the process 600 may follow the "NO" route from block 614 to iterate the determination at block 614 until a specified timestamp is reached. If the playback of the media data 126 has reached a timestamp (e.g., the first timestamp) that is specified in the command data 128 as being associated with a particular operation(s), the process 600 may follow the "YES" route from block 614 to block 616.

At 616, the device 110, via the client application 154, may perform one or more operation that are specified in the command data 128 and are associated with the timestamp (e.g., the first timestamp) that has been reached in the playback of the media data 126. The operation(s) performed at block 616 can vary, as indicated by sub-blocks 618 and 620.

Consider an example where a first timestamp specified in the command data 128 has been reached at block 614. At sub-block 618, a first operation associated with the first timestamp in the command data 128 may include an operation of sending a command to a fitness apparatus 120 to control an aspect of output provided by the fitness apparatus 120. Because the sending of the command is driven by the first timestamp in the media data 126, the performance of this operation is in synchronization with a corresponding visual cue and/or auditory cue in the media content 302 that the user 112 sees and/or hears. If the fitness apparatus 120 is a stationary bicycle, output provided by the fitness apparatus 120 may be in the form of resistance to pedaling the bicycle, and the aspect of the output controlled by the command may include initiation of the resistance, cessation of the resistance, or adjustment of an intensity of the resistance. To illustrate the command may initiate resistance when the instructor 106 says "go!" in the media content 302 and starts pedaling hard with the initiated resistance. As shown by sub-block 619, the fitness apparatus 120 may comprise an EMS suit 320 worn by the user 112, and the output provided by the fitness apparatus 120 may comprise an electrical impulse(s) delivered via an electrode(s) of the EMS suit 320. In this EMS suit example, the command sent at sub-block 618 may control an aspect of the electrical impulse(s) delivered via the electrode(s) of the EMS suit 320, such as by controlling the initiation of the electrical impulse(s), the cessation of the electrical impulse(s), or the adjustment of an intensity of the electrical impulse(s). It is to be appreciated that, when the device 110 is separate from the fitness apparatus 120, such as a tablet computer used by the user 112 while wearing an EMS suit 320, the sending of the command to the fitness apparatus 120 at sub-block 618 may include wirelessly sending the command via a wireless radio of the device 110 to the fitness apparatus 120, which may have its own wireless receiver (e.g., an impulse pack 300 of the EMS suit 320 with a wireless receiver, such as a Bluetooth radio).

At sub-block 620, a second operation associated with the first timestamp in the command data 128 that was reached at block 614 may include an operation of causing presentation of graphical information 502 overlaying the media content 302 on the display that is outputting the media content 302. Examples of graphical information 502 that can be overlaid atop the media content 302 are shown in FIG. 5, and may relate to the current exercise movement, a time remaining until a next exercise movement or a next rest period, the output of the fitness apparatus 120 (e.g., if an electrical impulse is on or off), etc.

At 622, a determination may be made as to whether the playback of the media data 126 should be stopped. For example, the playback may be stopped if the end of the playback has been reached, if the user 112 provides user input to stop or pause the playback, etc. If the playback of the media data 126 should be stopped, the process 600 may follow the "YES" route from block 622 to block 624 where the playback of the media data 126 may be stopped. If the playback should not be stopped (e.g., if there is time remaining in the playback and if the user 112 has not requested to stop or pause the playback), the process 600 may follow the "NO" route from block 622 back to block 614 where the device 110 may determine whether the playback of the media data 126 has reached a subsequent timestamp of the timestamps specified in the command data 128 that is associated with another operation(s) to be performed. Thus, the loop from block 622 to block 614 may iterate for multiple timestamps in the media data 126 that trigger operations to be performed, and, in this manner, the operations, driven by the timestamps in the media data 126 may be performed in synchronization with aspects of the media content 302 (e.g., in synchronization with visual and/or auditory cues of the instructor 106 featured in the media content 302).

Figure 7:
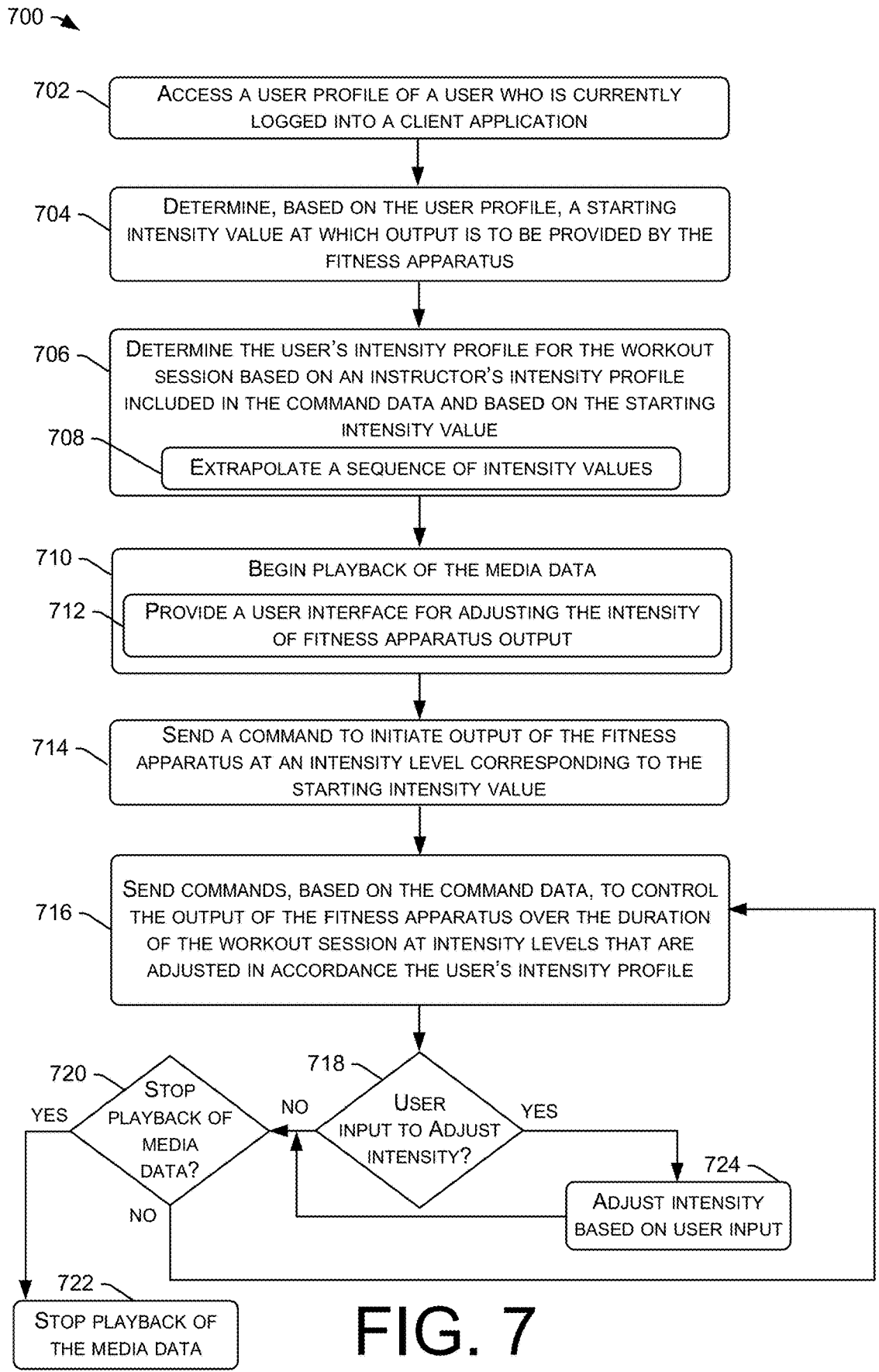
FIG. 7 is a flow diagram of an example process for creating a customized intensity profile of a user based on an instructor's intensity profile, and providing a user interface to the user for adjusting the intensity of the fitness apparatus output in real-time during a workout session.

FIG. 7 is a flow diagram of an example process 700 for determining an intensity profile of a user based on an instructor's intensity profile, and providing a user interface to the user for adjusting the intensity of the fitness apparatus output in real-time during a workout session. For discussion purposes, the process 700 is described with reference to the previous figures.

At 702, a device 110 may access a user profile 160 of a user 112 who is currently logged into a client application 154 executing on the device 110. At 704, the device 110 may determine, based at least in part on the user profile 160 of the user 112, a starting intensity value 404(2) at which output is to be provided by a fitness apparatus 120 of the user 112. The starting intensity value 404(2) may be based on a starting intensity value of a past (e.g., a previous) workout session, as indicated in the user profile 160, or it may be a default starting intensity value if there is no history on the user 112. Initially, the user 112 may navigate to a setup menu of the client application 154 to enter information such as body type, experience level, fitness condition, etc., which may be used by the client application 154 to select an appropriate starting intensity value at block 704 for output provided by the fitness apparatus 120. In some embodiments, the determination of the starting intensity value at block 704 may include determining a rate at which the intensity is to increase from zero to the starting intensity value 404(2). In some embodiments, this determination may include determining whether to ramp to the starting intensity value 404(2) or to provide output at the starting intensity value 404(2) without ramping. An example of ramping to the starting intensity value 404(2) is shown in FIG. 4. If it is determined to ramp to the starting intensity value 404(2), a determination at block 704 may be to determine the rate of increase to the starting intensity value 404(2). In some embodiments, the device 110 may determine to ramp in a smooth, linear fashion, or to increment the intensity in a stepwise manner over time at discrete intervals. In some embodiments, the device 110 may determine a spoken language in which to output audio content and/or graphical information that is to be overlaid atop the image content. This way, a user 112 can hear a translated version of the instructor's 106 audible instructions in a spoken language that the user 112 understands, and/or the user 112 can read text in graphical information 502 that is in the spoken language understood by the user 112.

At 706, the device 110 may determine, based at least in part on command data 128 associated with a workout session and the starting intensity value 404(2), an intensity profile 402(2) for the user 112. This intensity profile 402(2) determined at block 706 is to be used for controlling an intensity of the output of the fitness apparatus 120 during the workout session. The command data 128 may have been received from a remote system 108, as described herein, and may specify operations in the form of commands that are to be sent to the fitness apparatus 120 to control aspects of the output provided by the fitness apparatus 120, such as the intensity of the output. As such, the command data 128 may specify a first sequence of intensity values that represent an intensity profile 402(1) of an instructor 106 who is to be featured in media content that the user 112 is to consume during the workout session. In some embodiments, other parameters relating to the output of the fitness apparatus 120 may be determined at block 706, such as a pulse width parameter(s) that defines the duration(s) of the electrical impulses during the workout session, a frequency parameter(s) that defines of the frequency (or frequencies) of the electrical impulses during the workout session, and/or any other suitable parameter(s) relating to the output of the fitness apparatus 120. In some embodiments, one or more of these other parameters may be determined based on the type of workout session (e.g., explosive strength training vs. endurance training).

At sub-block 708, as part of determining the intensity profile 402(2) of the user 112, the device 110 may extrapolate a second sequence of intensity values based at least in part on the starting intensity value 404(2) determined at block 704, and based on the first sequence of intensity values that represents the instructor's 106 intensity profile 402(1). Because the user 112 is a different person than the instructor 106, the user's intensity profile 402(2) may differ from the instructor's 106 intensity profile 402(1). For instance, their starting intensity values 404 may be different, and, as such, the intensity of the fitness apparatus output may be different for each person for the same workout session. For example, individual intensity values of the user's 112 intensity profile 402(2) may be a fraction of, or a multiple of, corresponding intensity values of the instructor's 106 intensity profile 402(1). If, for instance, the instructor 106 is in better shape or more experienced than the user 112, the sequence of intensity values of the user's 112 intensity profile 402(2) may reflect the same adjustments at the same time as the instructor's 106 intensity profile 402(1), but the user's 112 intensity values may be at 50% of the instructor's 106 intensity values.

At 710, the device 110, via the client application 154, may begin playback of media data 126 for output of media content 302 on an output device (e.g., a peripheral system 158). The media data 126 may be associated with the command data 128 (e.g., they may relate to the same workout session), and the media content 302 may feature the instructor 106 conducting the workout session.

At sub-block 712, the device 110 may provide a user interface (e.g., a VUI, GUI, etc.) for adjusting the intensity of the output provided by the fitness apparatus 120. This user interface may be provided during (e.g., throughout) the playback of the media data 126 so that the user 112 can conveniently adjust the intensity of the output provided by the fitness apparatus 120 at one or more times during the workout session. In some embodiments, the user interface of the device 110 may provide other controls, such as a control for pausing the media playback (e.g., an icon that can be selected to pause the playback of the media data 126, and/or a control for requesting to stop following the instructor's 106 intensity profile 402(1). For example, the user 112 may request, at any time during the workout session, to stop following the instructor's 106 intensity profile 402(1), and, in response, the intensity of the output of the fitness apparatus 120 may remain constant for a remainder of the workout session, unless the user 112 adjusts the intensity manually or resumes following the instructor's 106 intensity profile 402(1). This may be useful if the user 112 is feeling tired in the middle of the workout session and believes that it is best to stop following the instructor's 106 intensity profile 402(1) without completely aborting the workout session.

In some embodiments, the device 110 may further cause presentation of the intensity profile 402(2) of the user 112 (and possibly additional intensity profiles 402 of the user 112 and/or of other users 112) as a graphic overlaying the media content 302 on the display, the intensity profile 402(2) being presented as a sequence of intensity values plotted over time. For example, the user's 112 intensity profile 402(2) for the current workout session may be presented with a previous intensity profile of the user 112 for a previous workout session performed by the user 112 in the past so that the user 112 can compete against himself/herself. Additionally, or alternatively, the user's 112 intensity profile 402(2) for the current workout session may be presented with an intensity profile of another user(s) 112 who is performing the workout session at the same time as the user 112, or who has performed the workout session in the past, while using another fitness apparatus 120.

At 714, the device 110 may send a first command to the fitness apparatus 120 to initiate the output of the fitness apparatus 120 at an intensity level corresponding to the starting intensity value 404(2) determined for the user 112. At 716, the device 110 may send, based at least in part on the command data 128, one or more second commands to the fitness apparatus 120 to control the intensity of the output of the fitness apparatus 120 in accordance with the intensity profile 402(2) of the user 112 during the workout session. Thus, the device 110 may send commands to the fitness apparatus 120 throughout the workout session to control the intensity of the fitness apparatus output at a level that is appropriate for the user 112, while also controlling the output of the fitness apparatus 120 in accordance with the sequence of operations specified in the command data 128 so that the output of the fitness apparatus 120 is synchronized with the media content 302. It is to be appreciated that, these operations may be driven by the timestamps in the media data 126, such as by implementing at least part of the process 600, such that the intensity of the output of the fitness apparatus 120 may be controlled (e.g., adjusted) at block 716 at appropriate times during the playback of the media data 126 (e.g., in synchronization with visual and/or auditory cues of the instructor 106 featured in the media content 302).

At 718, a determination may be made as to whether the device 110 has received user input to adjust the intensity of the output provided by the fitness apparatus 120 at any time during the workout session. If no user input is received at block 718, the process 700 may follow the "NO" route from block 718 to block 720, where a determination may be made as to whether the playback of the media data 126 should be stopped. For example, the playback may be stopped if the end of the playback has been reached, if the user 112 provides user input to stop or pause the playback, etc. If the playback of the media data 126 should be stopped, the process 700 may follow the "YES" route from block 720 to block 722 where the playback of the media data 126 may be stopped. If the playback should not be stopped (e.g., if there is time remaining in the playback and if the user 112 has not requested to stop or pause the playback), the process 700 may follow the "NO" route from block 720 back to block 716 where the device 110 may continue processing the command data 128 to send commands to control the intensity of the output provided by the fitness apparatus 120 in accordance with the operations specified in the command data 128. Thus, the loop from block 720 to block 716 may iterate throughout playback of the media data 126.

If, at block 718, user input has been received by the device 110 for adjusting the intensity of the output provided by the fitness apparatus 120, the process 700 may follow the "YES" route from block 718 to block 724, where the intensity of the fitness apparatus output may be adjusted by the device 110 sending a command to the fitness apparatus 120. The user interface provided at sub-block 712 may be in the form of a GUI that presents a first selectable element 162 and a second selectable element 164 on the display 156 of the device 110. The user 112 may select the first selectable element 162 to increase, at block 724, the current intensity level at which the output is provided by the fitness apparatus 120 to an increased intensity level, or the user 112 may select the second selectable element 164 to decrease, at block 724, the current intensity level at which the output is provided by the fitness apparatus 120 to a decreased intensity level. From block 724, the process 700 may proceed to block 720 where the process 700 either iterates to block 716, or stops the playback of the media data 126, as appropriate.

Figure 8:
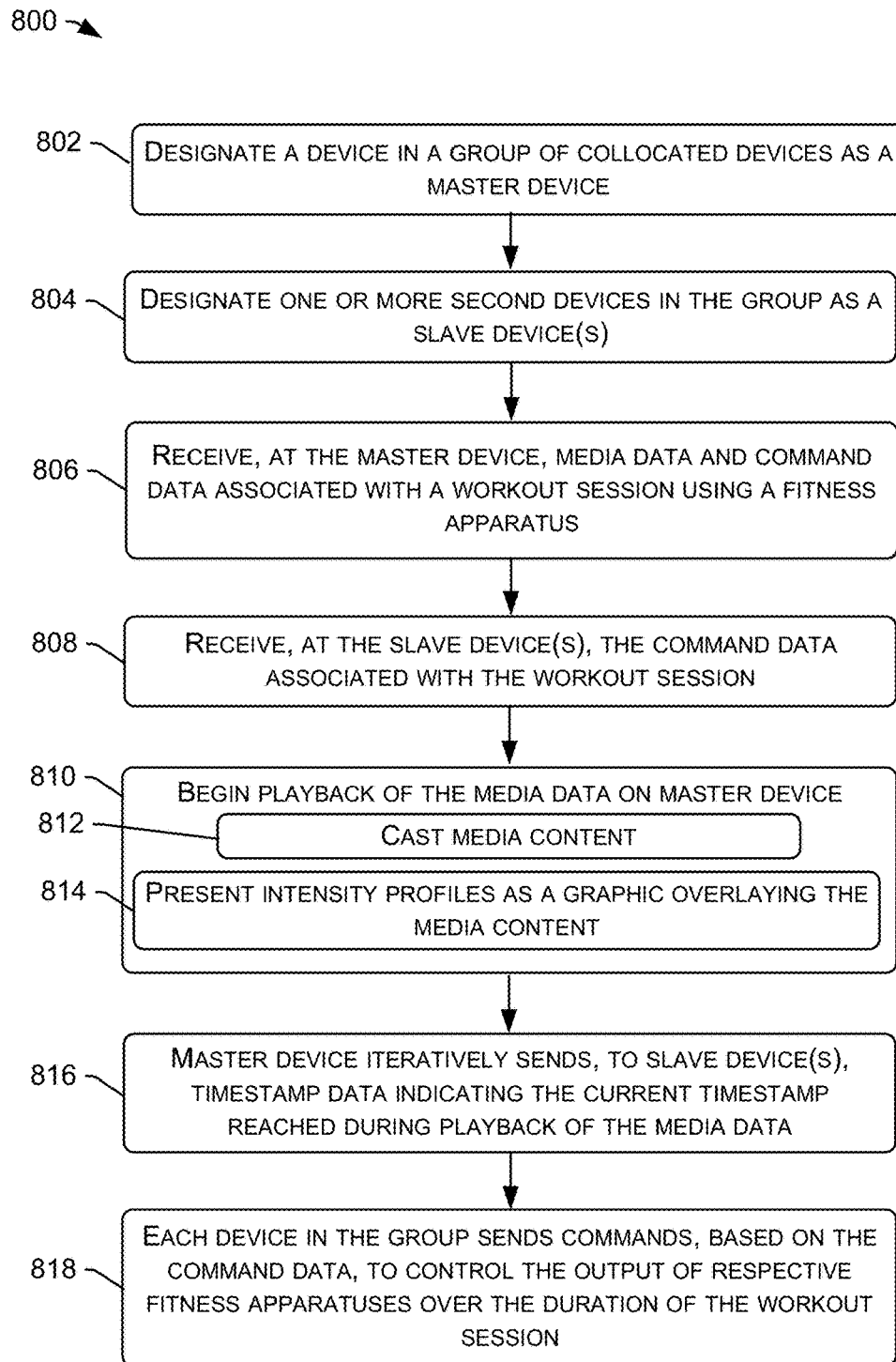
FIG. 8 is a flow diagram of an example process for synchronizing the output of a plurality of collocated fitness apparatuses with media content and for presenting intensity profiles on a display.

FIG. 8 is a flow diagram of an example process 800 for synchronizing the output of a plurality of collocated fitness apparatuses with media content and for presenting intensity profiles on a display. For discussion purposes, the process 800 is described with reference to the previous figures.

At 802, a first device 110(1) of a user 112, or the remote system 108, may designate the first device 110(1) as a master device among a group of devices 110 collocated in an environment 118. At 804, the first device 110(1), or the remote system 108, may designate one or more second devices 110(2), 110(3), etc. among the group of devices 110 as slave devices. The designations at blocks 802 and 804 may use any suitable criteria for designating a master and one or more slaves of a group of devices 110, such as designating the master and the slaves pursuant to a user's 112 request (i.e., letting the user 112 select which device 110 to be the master device and which device(s) 110 to be the slave device). The remote system 108, or a local device 110 may facilitate a throughput test to see which device 110 is in a suitable or optimal position to act as a master device. FIG. 1 shows an example arrangement of at least three devices 110 in a group that are collocated in the same environment 118.

At 806, the master device 110(1) may receive media data 126 and command data 128 associated with a workout session, where the workout session is to be performed by users 112 of the devices 110 while using respective fitness apparatuses 120. At 808, the slave device(s) 110(2), 110(3), etc. may receive the command data 128 associated with the workout session. The slave device(s) 110(2), 110(3), etc. may receive the command data 128 directly from the remote system 108 (e.g., via a wireless access point in the environment 118), or the slave device(s) 110(2), 110(3), etc. may receive the command data 128 from the master device 110 (e.g., over a WLAN). In either case, the slave device(s) 110(2), 110(3), etc. need not receive the media data 126, but, in some embodiments, the slave device(s) 110(2), 110(3), etc. may receive the media data 126 (e.g., if each device 110 in the group is to playback the media data 126 on respective displays thereof, in synchronization with each other).

At 810, the master device 110(1) may begin the playback the media data 126 associated with the workout session for output of the media content 302 on an output device. The client application 154 of the master device 110(1) may be utilized to playback the media data 126 at block 810. The output device may include the display 156 and/or speaker(s) of the master device 110(1). However, as shown by sub-block 812, the master device 110(1) may cast the media content 302 to the peripheral system, such as a peripheral display system 158, during the playback of the media data 126, which may be useful in a group setting where multiple users 112 are following along with the instructor 106 featured in the media content 302 at the same time. The client application 154 of the master device 110(1) may be used to cast the media content 302 to a peripheral system.

At sub-block 814, the master device 110(1) and the slave device(s) 110(2), 110(3), etc. may further cause presentation of the intensity profiles 402 of the users 112 as a graphic overlaying the media content 302 on the display of the output device. These intensity profiles 402 may be presented as a sequence of intensity values plotted over time for each user so that users 112 in the group can engage in friendly competition for a social aspect to the workout session.

At 816, the master device 110(1) may iteratively send timestamp data to the slave device(s) 110(2), 110(3), etc. during the playback of the media data 126 on the master device 110(1). This timestamp data may indicate a current timestamp reached during the playback of the media data 126 on the master device 110(1) so that the slave device(s) 110(2), 110(3), etc. can remain apprised of the current status or progress of the playback on the master device 110(1). The iterative sending of timestamp data may be performed using a unicast or a multicast communication technique. For example, the master device 110(1) may send unicast packets to each member of the group independently, or the master device 110(1) may send multicast packets to all slave devices 110(2) and 110(3), etc. in the group. In some embodiments, the master device 110(1) may receive acknowledgements of receipt of the broadcasted packets from slave devices 110(2), 110(3), etc. In other embodiments, the master device 110(1) may broadcast packets without receiving acknowledgements from the slave devices 110(2), 110(3), etc. In some embodiments, slave devices 110(2), 110(3), etc. are configured to listen for a multicast timestamp synchronization signal from the master device 110(1). In these embodiments, even if a single sync signal is not received by a slave device 110(2) or 110(3), the slave device's timer may continue to run, thereby avoiding interruptions. In other words, a local timer of a slave device can function as a backup if packets from the master device 110(1) are not received for a short period of time (e.g., if one or more packets are dropped). It is to be appreciated that a multicasting approach may help mitigate misalignment between slave devices 110(2), 110(3), etc., because the timestamp packets are sent in parallel and likely to be received by slave devices at substantially the same time, as opposed to packets being sent sequentially in a unicast approach.

At 818, each device 110 in the group of devices 110 may send commands, based on the command data 128 accessible to each device 110, to control aspects of the output provided by respective fitness apparatuses 120 over the duration of the workout session. That is, the master device 110(1) may send commands to the fitness apparatus 120(1) being used by the user 112(1), a first slave device 110(2) may send commands to the fitness apparatus 120(2) being used by the user 112(2), and a second slave device 110(3) may send commands to the fitness apparatus 120(3) being used by the user 112(3), as depicted in FIG. 1. In this manner, each fitness apparatus 120 used by each user 112 may provide output that is synchronized with the media content 302 being consumed by the users 112, as described herein. For example, the command data 128 may specify operations that are to be performed at particular timestamps within the media data 126 during playback of the media data 126. As such, by the master device 110(1) iteratively sending the timestamp data to the slave device(s) 110(2), 110(3), etc. during playback of the media data 126 on the master device 110(1), the operations (e.g., sending commands to fitness apparatuses 120) may be driven by the timestamps in the media data 126 to synchronize the fitness apparatus output with what the users 112 are seeing and/or hearing via the output device.

Figure 9:
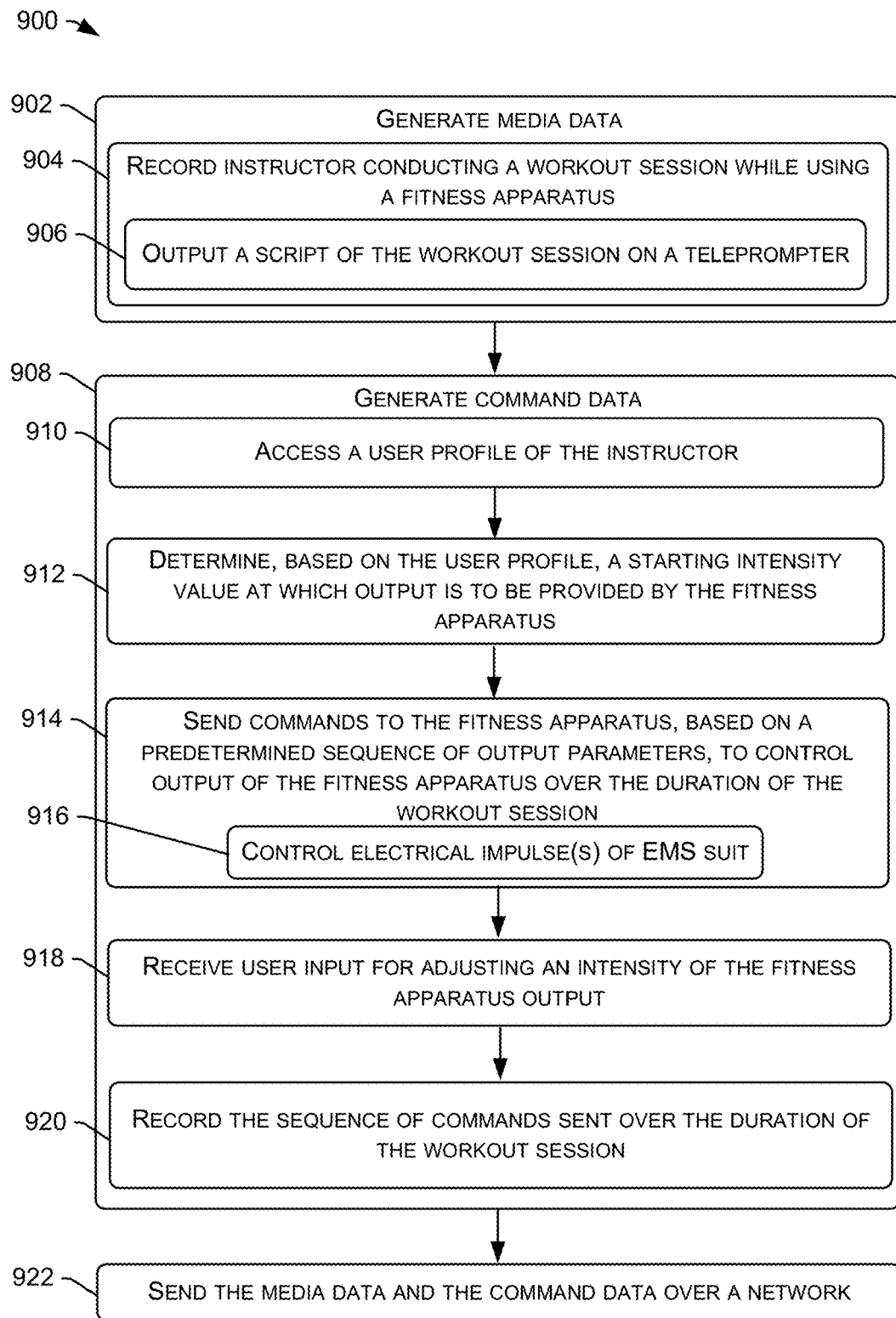
FIG. 9 is a flow diagram of an example process for generating media data and command data for a workout session, and sending the media data and the command data over a network for on-demand, or live, access by users of fitness apparatuses.

FIG. 9 is a flow diagram of an example process 900 for generating media data and command data for a workout session and sending the media data and command data over a network for on-demand, or live, access by users of fitness apparatuses. For discussion purposes, the process 900 is described with reference to the previous figures.

At 902, a recording device(s) 104 may be used to generate media data 126 corresponding to media content 302 featuring an instructor 106 conducting a workout session. For example, at sub-block 904, the recording device(s) 104 may be used to record an instructor 106 conducting a workout session while using a fitness apparatus 120(4). Furthermore, as shown by sub-block 906, a script 204 of the workout session may be output on a teleprompter 206 while the instructor 106 is conducting the workout session. This may cue the instructor 106 to deliver lines (e.g., verbal instructions, directions, guidance, recommendations, etc.) at the appropriate times, and/or to demonstrate exercise movements at the appropriate times, in accordance with the script 204.

At 908, a device 102 of the instructor 106 may execute a client application 136 that is used to generate command data 128 associated with the workout session. This command data 128 generally specifies operations that are to be performed by a computing device 110 of a user 112, and timestamps within the media data 126 at which the operations are to be performed during playback of the media data 126 on a computing device 110 of a user 112. In a live streaming scenario, the command data 128 may reference timestamps, or, in some cases, audio signatures, that are also provided in the output from the device 102 via an audio data stream. For instance, the device 102 may generate audio data that is to be sent as part of an audio data stream different from the audio data stream generated and output by the recording device(s) 104, and which may be used as a reference for determining a status or progress of the media data 126, when the media data 126 is being live streamed. In some embodiments, the timestamps provided in such an audio data stream may be tones at frequencies outside of the frequency band that is audible to the human ear, or other markers or signatures that can be placed in the audio data stream. In some embodiments, such timestamps may be encoded in the (first) audio data stream generated and output by the recording device(s) 104, such as by embedding inaudible tones or other markers/signatures in the first audio data stream. In some embodiments, such timestamps may be encoded in the video data stream itself. Various sub-operations may be involved in generating the command data 128 at block 908, as shown by the sub-blocks thereof.

At sub-block 910, the device 102 may access a user profile 138 of the instructor 106. The instructor 106 may be logged into the client application 136 to enable the client application 136 to access the user profile 138 of the instructor 106.

At sub-block 912, the device 102, via the client application 136, may determine, based at least in part on the user profile 138 of the instructor 106, a starting intensity value 404(1) at which the output is to be provided by the fitness apparatus 120(4) of the instructor 106. The starting intensity value 404(1) may be based on a starting intensity value of a past (e.g., a previous) workout session, as indicated in the user profile 138, or it may be a default starting intensity value if there is no history on the instructor 106. Initially, the instructor 106 may navigate to a setup menu of the client application 138 to enter information such as body type, experience level, fitness condition, etc., which may be used by the client application 138 to select an appropriate starting intensity value 404(1) at sub-block 912 for output provided by the fitness apparatus 120(4).

At sub-block 914, the device 102 of the instructor 106 may send, based at least in part on a predetermined sequence of output parameters, commands to the fitness apparatus 120(4) for controlling aspects of output provided by the fitness apparatus 120(4) over a duration of the workout session. In some embodiments, this may involve sending a command to initiate the output of the fitness apparatus 120(4) at an intensity level corresponding to the starting intensity value 404(1) determined at sub-block 912. As shown by sub-block 916, these commands may control aspects of electrical impulse delivered via electrodes of an EMS suit 220 worn by the instructor 106, if the fitness apparatus 120(4) is an EMS suit 220.

At sub-block 918, the device 102 of the instructor 106 may receive user input for adjusting an intensity of the output provided by the fitness apparatus 120(4) at one or more times during the workout session. For example, the device 102 may provide a user interface (e.g., a VUI, a GUI, etc.) to allow the instructor 106 to make adjustments to the intensity of the fitness apparatus 120(4) output, as desired.

At sub-block 920, the device 102, via the client application 136, may record the sequence of commands sent by the device 102 to the fitness apparatus 120(4) over the duration of the workout session to generate the command data 128. That is, the commands sent as a result of the predetermined sequence of output parameters, and the commands sent as a result of user input received for adjusting the intensity of the output provided by the fitness apparatus 120(4) may be recorded to generate a sequence of output parameters (including intensity level adjustments) that reflect what the instructor 106 experienced via the fitness apparatus 120(4) during the workout session. As some of the commands relate to intensity level adjustments for adjusting the intensity of the output provided by the fitness apparatus 120(4), the command data 128 may indicate a sequence of intensity values over the duration of the workout session that correspond to these intensity level adjustments. In other words, the command data 128 may reflect the intensity profile 402(1) of the instructor 106, which may be used to drive the intensity adjustments of the fitness devices 120 of users 112 when the media data 126 is played back on devices 110 of the users 112.

At 922, the device 102 of the instructor 106 may send the media data 126 and the command data 128 over a network 114. For example, the device 102 may send (e.g., upload) the media data 126 and the command data 128 to a remote system 108 for on-demand access by users 112. The command data 128 may be uploaded as a file(s), such as a JSON file(s), while the media data 126 may be uploaded as a different type of file(s), such as a video file(s) of any suitable format. In this manner, the media data 126 and the command data 128 may be accessed by users 112 on-demand when users 112 would like to follow along with the workout session. In some embodiments, the device 102 may send a live data stream of the media data 126 and the command data 128 at block 922. In a live streaming scenario, the timestamps included in the video data stream itself may be utilized as a reference by the client application 154 of the user's 112 device 110 to determine a status or progress of the live stream of media data 126 so that the client application 154 can determine which operations to perform and when to perform them, as specified in the live stream of command data 128. In some embodiments, the device 102 of the instructor 106 may output an additional/second audio data stream that includes the timestamps, or some other marker (e.g., audio signatures), for the client application 154 of the user's 112 device 110 to reference in order to determine the status or progress of the live stream of media data 126. In some embodiments, such timestamps may be encoded within the (first) audio data stream generated by the recording device 104, which carries the audio data corresponding to the instructor's 106 utterances and other noise in the instructor's 106 environment 116.

Figure 10:
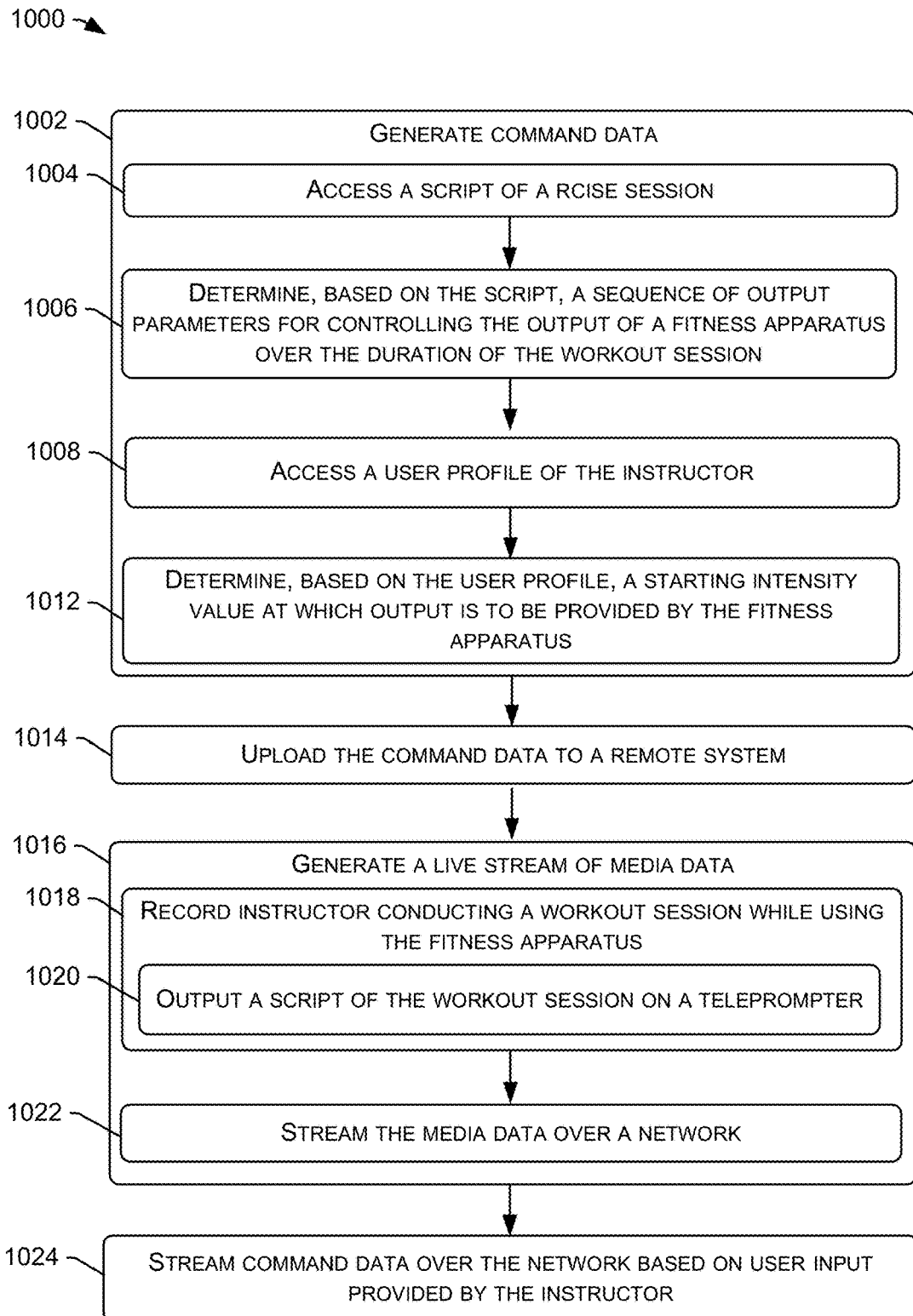
FIG. 10 is a flow diagram of an example process for live streaming an instructor conducting a workout session using a fitness apparatus, and for controlling output of a fitness apparatus(es) of a user(s) viewing the live stream of the instructor, according to another embodiment.

FIG. 10 is a flow diagram of an example process 1000 for live streaming an instructor conducting a workout session using a fitness apparatus and controlling output of a fitness apparatus(es) of a user(s) viewing the live stream of the instructor in synchronization with the instructor's visual demonstrations and verbal commands. For discussion purposes, the process 1000 is described with reference to the previous figures.

At 1002, a device 102 of an instructor 106 may execute a client application 136 that is used to generate command data 128 associated with a workout session that is to be live streamed to an audience of users 112 over a network 114. This command data 128 generally specifies operations that are to be performed by a computing device 110 of a user 112, and timestamps within the live stream of media data 126 at which the operations are to be performed during playback of the media data 126 on a computing device 110 of a user 112. Various sub-operations may be involved in generating the command data 128 at block 1002, as shown by the sub-blocks thereof.

At sub-block 1004, the device 102 of the instructor 106 may access a script 204 of the workout session. For example, the script 204 may outline phases of a workout, such as a warmup phase, an exercise phase, and a cool down phase, as well as exercise movements to be conducted throughout the session. This script 204 may be in a format that is able to be processed by the client application 136.

At sub-block 1006, the device 102 of the instructor, via the client application 136, may determine, based on the script 204 of the workout session, a sequence of output parameters for controlling the output of a fitness apparatus 120 over a duration of the workout session. For example, a sequence of output parameters may indicate when commands should be sent to the fitness apparatus 120 to initiate, cease, or adjust an intensity of the output provided by the fitness apparatus 120.

At sub-block 1008, the device 102 may access a user profile 138 of the instructor 106. The instructor 106 may be logged into the client application 136 to enable the client application 136 to access the user profile 138 of the instructor 106.

At sub-block 1012, the device 102, via the client application 136, may determine, based at least in part on the user profile 138 of the instructor 106, a starting intensity value 404(1) at which the output is to be provided by the fitness apparatus 120(4) of the instructor 106. The starting intensity value 404(1) may be based on a starting intensity value of a past (e.g., a previous) workout session, as indicated in the user profile 138, or it may be a default starting intensity value if there is no history on the instructor 106. Initially, the instructor 106 may navigate to a setup menu of the client application 138 to enter information such as body type, experience level, fitness condition, etc., which may be used by the client application 138 to select an appropriate starting intensity value 404(1) at sub-block 1012 for output provided by the fitness apparatus 120(4). With this data in-hand, the client application 136 can generate the command data 128 that reflects how and when (relative to timestamps in live streamed media data 126) a fitness apparatus 120 is to be controlled during the workout session.

At 1014, the device 102 of the instructor 106 may upload the command data 128 to a remote system 108 over a network 114. The command data 128 may be uploaded as a file(s), such as a JSON file(s). In this manner, the command data 128 may be accessed by users 112 on-demand when users 112 would like to follow along with a live stream of the workout session.

At 1016, a recording device(s) 104 may be used to generate a live stream of media data 126 corresponding to media content 302 featuring an instructor 106 conducting a workout session live in front of an audience of users 112 who are accessing the live stream using their respective computing devices 110. For example, at sub-block 1018, the recording device(s) 104 may be used to record the instructor 106 conducting the workout session while using a fitness apparatus 120(4). Furthermore, as shown by sub-block 1020, a script 204 of the workout session may be output on a teleprompter 206 while the instructor 106 is conducting the workout session. This may cue the instructor 106 to deliver lines (e.g., verbal instructions, directions, guidance, recommendations, etc.) at the appropriate times, and/or to demonstrate exercise movements at the appropriate times, in accordance with the script 204.

At 1022, the recording device(s) 104, and/or the computing device 102 (while in communication with the recording device(s), may send the live stream of the media data 126 over the network 114, the live stream of the media data 126 including the timestamps that are used to drive the performance of the operations specified in the command data 128 so that the output provided by the fitness apparatuses 120 of the users 112 is provided in synchronization with the instructor's 106 visual and auditory cues exhibited in the media content 302 the users 112 are seeing and/or hearing. The timestamps may be provided in the live stream of media data 126 by providing the timestamps in a secondary audio data stream (e.g., an audio data stream that is typically reserved for an auxiliary audio out on the output devices of the users 112). Alternatively, the timestamps may be provided in the video data stream of the live data stream.

At 1024, the device 102 of the instructor 106 may receive user input for adjusting an intensity of the output provided by the fitness apparatus 120(4) of the instructor 106 at one or more times during the workout session, and the device 102 may send a live stream of (second) command data over the network 114 that corresponds to these adjustments of the intensity of the output so that commands may be send by devices 110 of users 112 to adjust the intensity of the output of the fitness apparatuses 120 of the participating users 112 in a commensurate fashion. For example, the intensity level adjustments on the user-end may be customized to the user 112 (e.g., if the user 112 is running at 50% of the intensity of the instructor 106, the adjustment to the intensity of the output of the user's fitness apparatus 120 may be weighted accordingly).

Figure 11:
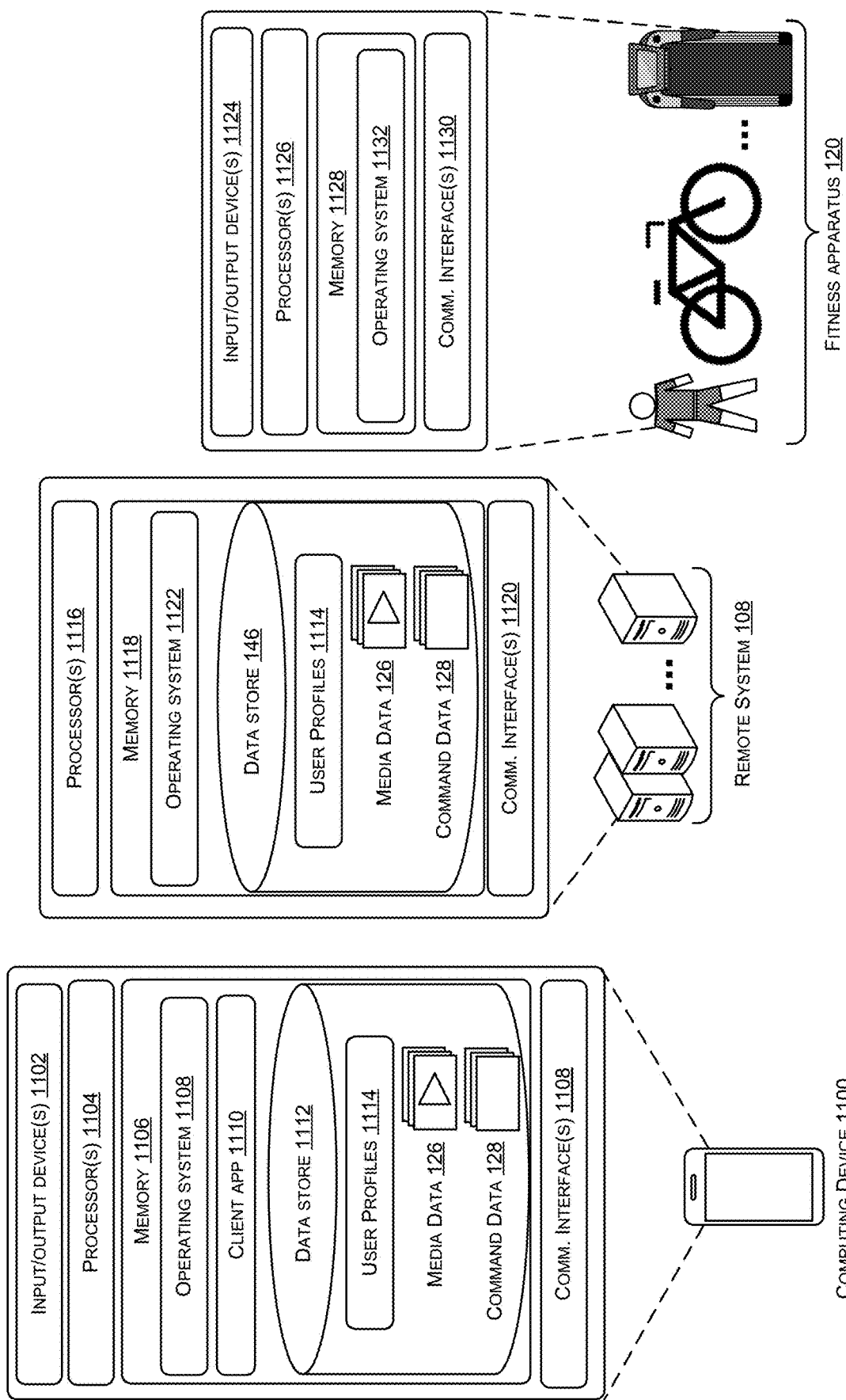
FIG. 11 illustrates block diagrams of computer components implemented at a personal computing device, a computing device(s) of a remote system, and a fitness apparatus, according to embodiments described herein.

FIG. 11 illustrates block diagrams of computer components implemented at a personal computing device 1100, a computing device(s) of a remote system 108, and a fitness apparatus 120, according to embodiments described herein. Starting with the computing device 1100, the computing device 1100 may represent either of the computing device 102 or the computing device 110 introduced in FIG. 1. Accordingly, the computing device 1100 may be used by an instructor 106 or by a user 112, as described herein. As shown in FIG. 11, the computing device 1100 may include one or more input/output (I/O) devices 1102, such as the controls (e.g., joysticks, trackpads, triggers, depressible buttons, etc.), potentially any other type of input or output devices. For example, the I/O devices 1102 may include one or more microphones to receive audio input, such as user voice input. In some implementations, one or more cameras or other types of sensors may function as input devices to receive gestural input, such as motion of the computing device 1100. In some embodiments, additional input devices may be provided in the form of a keyboard, keypad, mouse, touch screen, joystick, control buttons and the like. The input device(s) may further include control mechanisms, such as basic volume control button(s) for increasing/decreasing volume, as well as power and reset buttons.

The output devices, meanwhile, may include a display(s), a light element (e.g., LED), a vibrator to create haptic sensations, a speaker(s) (e.g., headphones), and/or the like. While a few examples have been provided, the computing device 1100 may additionally or alternatively comprise any other type of output device. In some instances, output by the one or more output devices may be based on input received by one or more of the input devices. For example, actuation of a control or the touchscreen may result in the output of a haptic response by a vibrator located adjacent (e.g., underneath) the control, the touchscreen, or at any other location.

The computing device 1100 is shown as including one or more processors 1104, memory 1106 (or non-transitory computer-readable media 1106), and a communications interface(s) 1108. These components may be implemented similarly to the processor(s) 130, memory 132, and communication interface(s) 134 described with reference to the computing device 102, and, as such, details of these components will not be explained again for the sake of brevity, as the description of the processor(s) 130, memory 132, and communication interface(s) 134 may be referenced herein to understand example implementations of the processor(s) 1104, memory 1106, and communication interface(s) 1108. Several modules such as instruction, datastores, and so forth may be stored within the memory 1106 and configured to execute on the processor(s) 1104. A few example functional modules are shown as stored in the memory 1106 and executed on the processor(s) 1104, although the same functionality may alternatively be implemented in hardware, firmware, or as a SOC.

An operating system module 1108 may be configured to manage hardware within and coupled to the computing device 1100 for the benefit of other modules. In addition, the memory 1106 may store a client application 1110, which may represent the client app 136 or the client app 154 described herein. The memory 1106 may further include a data store 1112, which may store one or more user profiles 1114, such as a user profile 1114 of a user 112 who has logged into the client application 1110 in the past, as well as media data 126 and/or command data 128 generated by the computing device 1100 or received (e.g., downloaded) from the remote system 108.

Turning to the remote system 108, the remote system 108 is shown as including one or more processors 1116, memory 1118 (or non-transitory computer-readable media 1118), and a communications interface(s) 1120. These components may be implemented similarly to the processor(s) 130, memory 132, and communication interface(s) 134 described with reference to the computing device 102, and, as such, details of these components will not be explained again for the sake of brevity, as the description of the processor(s) 130, memory 132, and communication interface(s) 134 may be referenced herein to understand example implementations of the processor(s) 1116, memory 1118, and communication interface(s) 1120. Several modules such as instruction, datastores, and so forth may be stored within the memory 1118 and configured to execute on the processor(s) 1116. A few example functional modules are shown as stored in the memory 1118 and executed on the processor(s) 1116, although the same functionality may alternatively be implemented in hardware, firmware, or as a SOC.

An operating system module 1122 may be configured to manage hardware within and coupled to computing device(s) of the remote system 108 for the benefit of other modules. In addition, the memory 1118 include the data store 146 introduced in FIG. 1, which may store one or more user profiles 1114 of users 112 who have registered with the remote system 108 as part of a service for accessing media data 126 and command data 128 to follow along with an instructor 106 featured in media content 302 who is conducting a workout session. The data store 146 may also maintain media data 126 and/or command data 128 generated by the computing devices 1100 of instructors for on-demand access by users 112. Furthermore, the remote system 108 may provide functionally for streaming live media data 126 of instructors to one or more users 112 over a network 114.

Turning to the fitness apparatus 120, the fitness apparatus 120 may include, without limitation, a wearable fitness apparatus (e.g., an EMS suit, a fitness watch, a fitness band, etc.), a treadmill, a stationary bicycle, an elliptical machine, a rowing machine, a stair climber, an exercise pool (e.g., a swimming machine), a weight machine, and/or any other similar type of fitness apparatuses 120. The fitness apparatus 120 is shown as including one or more input/output (I/O) devices 1124, such as the controls (e.g., joysticks, trackpads, triggers, depressible buttons, etc.), potentially any other type of input or output devices. For example, the I/O devices 1124 may include one or more microphones to receive audio input, such as user voice input. In some implementations, one or more cameras or other types of sensors may function as input devices to receive gestural input, such as motion of the fitness apparatus 120. In some embodiments, additional input devices may be provided in the form of a keyboard, keypad, mouse, touch screen, joystick, control buttons and the like.

The output devices, meanwhile, may include electrodes, belts, wheels, motors, resistance mechanisms (e.g., brakes, counterweights, etc.), fans, display(s), light element (e.g., LED), a vibrator to create haptic sensations, a speaker(s) (e.g., headphones), and/or the like. At least some of these output devices may provide the output of the fitness apparatus 120 described herein, which may be controlled via commands received from the computing device 1100 in various aspects. For example, electrical impulses may be delivered via electrodes (i.e., output devices) and controlled via commands received from the computing device 110 (e.g., to control initiation, cessation, duration, channels, and/or intensity of the electrical impulses). While a few examples have been provided, the fitness apparatus 120 may additionally or alternatively comprise any other type of output device. In some instances, output by the one or more output devices may be based on input received by one or more of the input devices. For example, actuation of a control or the touchscreen may result in the output of a haptic response by a vibrator located adjacent (e.g., underneath) the control, the touchscreen, or at any other location.

The fitness apparatus 120 is shown as including one or more processors 1126, memory 1128 (or non-transitory computer-readable media 1128), and a communications interface(s) 1130. These components may be implemented similarly to the processor(s) 130, memory 132, and communication interface(s) 134 described with reference to the computing device 102, and, as such, details of these components will not be explained again for the sake of brevity, as the description of the processor(s) 130, memory 132, and communication interface(s) 134 may be referenced herein to understand example implementations of the processor(s) 1126, memory 1128, and communication interface(s) 1130. In one example where the fitness apparatus 120 comprises an EMS suit 220/320, some or all of these components may be provided in an impulse pack 200/300 situated in or on the EMS suit 220/300, as depicted in FIGS. 2 and 3. Several modules such as instruction, datastores, and so forth may be stored within the memory 1128 and configured to execute on the processor(s) 1126. A few example functional modules are shown as stored in the memory 1128 and executed on the processor(s) 1126, although the same functionality may alternatively be implemented in hardware, firmware, or as a SOC. An operating system module 1132 may be configured to manage hardware within and coupled to the fitness apparatus 120 for the benefit of other modules.

The environment and individual elements described herein may of course include many other logical, programmatic, and physical components, of which those shown in the accompanying figures are merely examples that are related to the discussion herein.

Other architectures may be used to implement the described functionality, and are intended to be within the scope of this disclosure. Furthermore, although specific distributions of responsibilities are defined above for purposes of discussion, the various functions and responsibilities might be distributed and divided in different ways, depending on circumstances.

Furthermore, although the subject matter has been described in language specific to structural features and/or methodological acts, it is to be understood that the subject matter defined in the appended claims is not necessarily limited to the specific features or acts described. Rather, the specific features and acts are disclosed as exemplary forms of implementing the claims.

Although the subject matter has been described in language specific to structural features and/or methodological acts, it is to be understood that the subject matter defined in the appended claims is not necessarily limited to the specific features or acts described. Rather, the specific features and acts are disclosed as illustrative forms of implementing the claims.

What is claimed is:

1. A device comprising:
   a processor; and
   memory storing computer-executable instructions that, when executed by the processor, cause the device to:
   access a user profile of a user who is currently logged into a client application executing on the device;
   determine, based at least in part on the user profile of the user, a starting overall intensity level, wherein overall intensity level corresponds to intensity values at which electrical impulses are delivered to the user, at relative intensity offsets, via electrodes of an electrical muscle stimulation (EMS) suit of the user;
   determine, based at least in part on the starting overall intensity level and on command data associated with a workout session, an intensity profile of the user, wherein the intensity profile of the user represents a first sequence of overall intensity levels used for controlling intensities of the electrical impulses delivered via the electrodes of the EMS suit during the workout session;
   begin playback of media data to cause output of media content on an output device, the media data associated with the command data, and the media content featuring an instructor conducting the workout session;
   send a first command to the EMS suit to initiate delivering the electrical impulses via the electrodes of the EMS suit at the relative intensity offsets in accordance with the starting overall intensity level; and
   send, based at least in part on the command data, one or more second commands to the EMS suit to control the intensities of the electrical impulses delivered via the electrodes of the EMS suit in accordance with the intensity profile of the user during the workout session.

2. The device of claim 1, wherein:
   the command data specifies a second sequence of overall intensity levels that represents an intensity profile of the instructor; and
   determining the intensity profile of the user comprises extrapolating the first sequence of overall intensity levels based at least in part on the starting overall intensity level and the second sequence of overall intensity levels.

3. The device of claim 2, wherein a first overall intensity level of the first sequence of overall intensity levels is a fraction of, or a multiple of, a first overall intensity level of the second sequence of overall intensity levels.

4. The device of claim 1, wherein the output device comprises a display, and wherein the computer-executable instructions, when executed by the processor, further cause the device to cause presentation of the intensity profile of the user as a graphic overlaying the media content on the display, the intensity profile of the user being presented as the first sequence of overall intensity levels plotted over time.

5. The device of claim 4, wherein the intensity profile of the user is a first intensity profile, and wherein the computer-executable instructions, when executed by the processor, further cause the device to cause presentation of a second intensity profile as a second graphic overlaying the media content on the display, the second intensity profile being presented as a third sequence of overall intensity levels plotted over time, and wherein the second intensity profile is associated with at least one of:
   a previous workout session performed by the user; or
   another user who is performing, or has performed, the workout session while using another fitness apparatus.

6. The device of claim 1, further comprising a display, wherein the computer-executable instructions, when executed by the processor, further cause the device to present on the display, during the playback of the media data:
   a first selectable element that, upon selection, causes the device to send a third command to the EMS suit to decrease a current overall intensity level at which the electrical impulses are delivered via the electrodes of the EMS suit; and
   a second selectable element that, upon selection, causes the device to send a fourth command to the EMS suit to increase the current overall intensity level.

7. The device of claim 1, wherein:
   the command data specifies:
   operations, at least some of the operations comprising operations for sending the one or more second commands to the EMS suit; and
   timestamps within the media data at which the operations are to be performed during the playback of the media data on the device; and
   the computer-executable instructions, when executed by the processor, further cause the device to:
   determine that the playback of the media data has reached a timestamp of the timestamps specified in the command data; and
   perform an operation, of the operations specified in the command data, associated with the timestamp, wherein the operation comprises sending a command, of the one or more second commands, to the EMS suit.

8. The device of claim 1, wherein the computer-executable instructions, when executed by the processor, further cause the device to determine a rate at which to increase from zero to the starting overall intensity level.

9. A method comprising:
   accessing, by a device executing a client application, a user profile of a user who is currently logged into the client application;
   determining, based at least in part on the user profile of the user, a starting overall intensity level, wherein overall intensity level corresponds to intensity values at which electrical impulses are delivered to the user, at relative intensity offsets, via electrodes of an electrical muscle stimulation (EMS) suit of the user;
   determining, based at least in part on the starting overall intensity level and on command data associated with a workout session, an intensity profile of the user, wherein the intensity profile of the user represents a first sequence of overall intensity levels used for controlling intensities of the electrical impulses delivered via the electrodes of the EMS suit during the workout session;
   beginning playback of media data to cause output of media content on an output device, the media data associated with the command data, and the media content featuring an instructor conducting the workout session;
   sending, by the device, a first command to the EMS suit to initiate delivering the electrical impulses via the electrodes of the EMS suit at the relative intensity offsets in accordance with the starting overall intensity level; and
   sending, by the device, and based at least in part on the command data, one or more second commands to the EMS suit to control the intensities of the electrical impulses delivered via the electrodes of the EMS suit in accordance with the intensity profile of the user during the workout session.

10. The method of claim 9, wherein the output device comprises a display, the method further comprising causing presentation of the intensity profile of the user as a graphic overlaying the media content on the display, the intensity profile of the user being presented as the first sequence of overall intensity levels plotted over time.

11. The method of claim 10, wherein the intensity profile of the user is a first intensity profile, the method further comprising causing presentation of a second intensity profile as a second graphic overlaying the media content on the display, the second intensity profile being presented as a third sequence of overall intensity levels plotted over time, and wherein the second intensity profile is associated with at least one of:
   a previous workout session performed by the user; or
   another user who is performing, or has performed, the workout session while using another fitness apparatus.

12. The method of claim 9, wherein:
   the command data specifies a second sequence of overall intensity levels that represents an intensity profile of the instructor; and
   the determining of the intensity profile of the user comprises extrapolating the first sequence of overall intensity levels based at least in part on the starting overall intensity level and the second sequence of overall intensity levels.

13. The method of claim 9, further comprising causing the device to present on a display of the device, during the playback of the media data:
   a first selectable element that, upon selection, causes the device to send a third command to the EMS suit to decrease a current overall intensity level at which the electrical impulses are delivered via the electrodes of the EMS suit; and
   a second selectable element that, upon selection, causes the device to send a fourth command to the EMS suit to increase the current overall intensity level.

14. The method of claim 9, wherein:
   the command data specifies:
   operations, at least some of the operations comprising operations for sending the one or more second commands to the EMS suit; and
   timestamps within the media data at which the operations are to be performed during the playback of the media data on the device; and the method further comprises:
determining that the playback of the media data has reached a timestamp of the timestamps specified in the command data; and
performing an operation, of the operations specified in the command data, associated with the timestamp, wherein the operation comprises sending a command, of the one or more second commands, to the EMS suit.

15. The method of claim 9, further comprising determining to ramp to the starting overall intensity level.

16. One or more non-transitory computer-readable media storing computer-executable instructions that, when executed by a processor of a device, cause the device to:
access a user profile of a user who is currently logged into a client application executing on the device;
determine, based at least in part on the user profile of the user, a starting overall intensity level, wherein overall intensity level corresponds to intensity values at which electrical impulses are delivered to the user, at relative intensity offsets, via electrodes of an electrical muscle stimulation (EMS) suit of the user;
determine, based at least in part on the starting overall intensity level and on command data associated with a workout session, an intensity profile of the user, wherein the intensity profile of the user represents a first sequence of overall intensity levels used for controlling intensities of the electrical impulses delivered via the electrodes of the EMS suit during the workout session;
begin playback of media data to cause output of media content on an output device, the media data associated with the command data, and the media content featuring an instructor conducting the workout session;
send a first command to the EMS suit to initiate delivering the electrical impulses via the electrodes of the EMS suit at the relative intensity offsets in accordance with the starting overall intensity level; and
send, based at least in part on the command data, one or more second commands to the EMS suit to control the intensities of the electrical impulses delivered via the electrodes of the EMS suit in accordance with the intensity profile of the user during the workout session.

17. The one or more non-transitory computer-readable media of claim 16, wherein:
the command data specifies a second sequence of overall intensity levels that represents an intensity profile of the instructor; and
determining the intensity profile of the user comprises extrapolating the first sequence of overall intensity levels based at least in part on the starting overall intensity level and the second sequence of overall intensity levels.

18. The one or more non-transitory computer-readable media of claim 16, wherein the output device comprises a display, and wherein the computer-executable instructions, when executed by the processor, further cause the device to cause presentation of the intensity profile of the user as a graphic overlaying the media content on the display, the intensity profile of the user being presented as the first sequence of overall intensity levels plotted over time.

19. The one or more non-transitory computer-readable media of claim 16, wherein the computer-executable instructions, when executed by the processor, further cause the device to present on a display of the device, during the playback of the media data:
a first selectable element that, upon selection, causes the device to send a third command to the EMS suit to decrease a current overall intensity level at which the electrical impulses are delivered via the electrodes of the EMS suit; and
a second selectable element that, upon selection, causes the device to send a fourth command to the EMS suit to increase the current overall intensity level.

20. The one or more non-transitory computer-readable media of claim 16, wherein the client application is paired with a peripheral device, and the starting overall intensity level is determined based at least in part on attributes of the user determined from data the client application received from the peripheral device.

* * * * *